United States Patent
Barron et al.

(10) Patent No.: US 8,575,548 B2
(45) Date of Patent: Nov. 5, 2013

(54) ANALYZING THE TRANSPORT OF PLASMONIC PARTICLES THROUGH MINERAL FORMATIONS

(75) Inventors: Andrew R. Barron, Houston, TX (US); Samuel J. Maguire-Boyle, Drogheda (IE); Alvin White Orbaek, Dublin (IE)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 13/701,769

(22) PCT Filed: Jun. 2, 2011

(86) PCT No.: PCT/US2011/038925
§ 371 (c)(1),
(2), (4) Date: Mar. 15, 2013

(87) PCT Pub. No.: WO2011/153347
PCT Pub. Date: Dec. 8, 2011

(65) Prior Publication Data
US 2013/0168543 A1    Jul. 4, 2013

Related U.S. Application Data

(60) Provisional application No. 61/350,836, filed on Jun. 2, 2010.

(51) Int. Cl.
*H01J 37/05* (2006.01)
*H01J 37/28* (2006.01)
*G01N 33/62* (2006.01)

(52) U.S. Cl.
USPC ........... 250/306; 250/259; 250/305; 250/307; 250/461.2; 436/108

(58) Field of Classification Search
USPC ........ 250/259, 461.2, 305, 306, 307; 436/180
See application file for complete search history.

(56) References Cited

U.S. PATENT DOCUMENTS

| 5,023,139 A | 6/1991 | Birnboim et al. |
| 7,082,993 B2 | 8/2006 | Ayoub et al. |

(Continued)

FOREIGN PATENT DOCUMENTS

WO    2009108921    9/2009

OTHER PUBLICATIONS

International Searching Authority; International Search Report and Written Opinion for PCT/US2011/038925; Sep. 29, 2011.

(Continued)

*Primary Examiner* — David Porta
*Assistant Examiner* — Kenneth J Malkowski
(74) *Attorney, Agent, or Firm* — Winstead PC

(57) ABSTRACT

A transport of plasmonic particles through a mineral formation is analyzed by flowing a plasmonic particles solution through an immobile phase (e.g., a mineral formation), determining an absorbance of the plasmonic particles solution subsequent to flowing the plasmonic particles solution through the immobile phase, comparing the determined absorbance of the plasmonic particles solution with an absorbance of the plasmonic particles solution determined previous to flowing the plasmonic particles solution through the immobile phase, and determining an absorbance of the plasmonic particles to the immobile phase as a function of the comparison. The plasmonic particles solution may be produced by dissolving or suspending plasmonic particles in a mobile phase. Flowing the plasmonic particles solution through the immobile phase may include injecting the plasmonic particles solution into the immobile phase, and then flushing the plasmonic particles solution through the immobile phase.

18 Claims, 36 Drawing Sheets

(56) References Cited

U.S. PATENT DOCUMENTS

| | | | |
|---|---|---|---|
| 2004/0197929 A1* | 10/2004 | Lagwinski et al. | 436/180 |
| 2005/0274510 A1 | 12/2005 | Nguyen et al. | |
| 2006/0011862 A1* | 1/2006 | Bernstein | 250/461.2 |
| 2006/0102345 A1 | 5/2006 | McCarthy et al. | |

OTHER PUBLICATIONS

Song, Kyungjum et al., "Surface Plasmon Dynamics of a Metallic Nano-Particle," Aug. 2-5, 2007, Nanotechnology, IEEE-NANO 2007, 7th IEEE Conference.

Barron, Andrew R., et al., "Nanotechnology for the Oil and Gas Industry," Rice University, Houston, Texas, 2008.

Lee, J. P. C.; Meisel, D.; "Adsorption and surface-enhanced Raman of dyes on silver and gold sols" J. Phys. Chem. 1982, 86, 17, 3391-3395.

Kimura, K.; Yao, H.; Sato, S. "Self-Assembling of Gold and Silver Nanoparticles at a Hydrophilic/Hydrophobic Interface: A Synthetic Aspect and Superstructure Formation" Synthesis and Reactivity in Inorganic, Metal-Organic, andNano-Metal Chemistry 2006, 36, 3, 237-264.

Zhao, Y.; Jiang, Y.; Fang, Y.; "Spectroscopy property of Ag nanoparticles" Spectrochimica Acta Part A 2006, 65,1003-1006.

Evanoff, D. D.; Chumanov, G. "Synthesis and Optical Properties of Silver Nanoparticles and Arrays" ChemPhysChem 2005, 6, 1221-1231.

Callender, R.L., C. J. Harlan, N. M. Shapiro, C. D, Jones, D. L. Callahan, M. R. Wiesner, R. Cook, and A. R. Barron, "Aqueous synthesis of water soluble alumoxanes: environmentally benign precursors to alumina and aluminum-based ceramics", Chem. Mater., 1997, 9,2418.

Jones, C. D., A. R. Barron, M. R. Wiesner, and J.-Y. Bottero, "Synthesis and characterization of carboxylate-FeOOH nanoparticles (ferroxanes) and ferroxane-derived ceramics", J, Rose, M. M. Cortalezzi-Fidalgo, S. Moustier, C. Magnetto, Chem. Mater., 2002,14, 621.

Zeng, L., L. Zhang, and A. R. Barron, "Tailoring aqueous solubility of functionalized single-wall carbon nanotuhes over a wide pH range through substituent chain length." Nano Lett., 2005, 5, 2001.

Landry, C. C., N, Pappe, M. R. Mason, A. W. Apblett, A. N. Tyler, A. N. MacInnes, and A. R. Barron, "From minerals to materials: synthesis of alumoxanes from the reaction of boehmite with carboxylic acids." J. Mater. Chem., 1995, 5, 331.

Happel, J., "Viscous Flow in Multiparticle Systems: Slow Motion of Fluids Relative to Beds of Spherical Particles," AIChE J. 1958,4, 197.

Derjaguin, B. V. and L. D. Landau, "Theory of the Stability of Strongly Charged Lyophobic Sols and of the Adhesion of Strongly Charged Particles in Solutions of Electrolytes," USSR Acta Physicochim. 1941,14,633.

Rajagopalan, R. and C. Tien, "Trajectory Analysis of Deep-Bed Filtration with the Sphere-in-cell Porous Media Model," AICHe J. 1976,22, 523.

Yao, K. M., M. T. Habibian and C. R. O'Melia, "Water and Waste Water Filtration: Concepts and Applications," Environ. Sci. Technol. 1971,5,1105.

Elimelech, M., "Effect of particle size on the kinetics of particle deposition under attractive double layer interactions" J. Colloid Interface Sci. 1994,164,190.

Okkyong, C., et al., "The inhibitory effects of silver nanoparticles, silver ions, and silver chloride colloids on microbial growth," Water Research, 2008 (42):3066.

Tufenkji, N., et al., "Correlation Equation for Predicting Single-Collector Efficiency in Physicochemical Filtration in Saturated Porous Media," Environ. Sci. Technol. 2004, 38, 529.

Tobiason, J.E., et al., "Physicochemical Aspects of Particle Removal in Depth Filtration," J. Am. Water Works Assoc. 1988, 80, 54.

* cited by examiner

A

B

US 8,575,548 B2

ANALYZING THE TRANSPORT OF PLASMONIC PARTICLES THROUGH MINERAL FORMATIONS

CROSS-REFERENCE TO RELATED APPLICATIONS

This application claims priority to U.S. Provisional Patent Application No. 61/350,836, filed on Jun. 2, 2010, which is hereby incorporated by reference.

BRIEF SUMMARY

Embodiments of the present invention analyze a transport of plasmonic particles through a mineral formation by flowing a plasmonic particles solution through an immobile phase (e.g., a mineral formation), determining an absorbance of the plasmonic particles solution subsequent to flowing the plasmonic particles solution through the immobile phase, comparing the determined absorbance of the plasmonic particles solution with an absorbance of the plasmonic particles solution determined previous to flowing the plasmonic particles solution through the immobile phase, and determining an absorbance of the plasmonic particles to the immobile phase as a function of the comparison. The plasmonic particles solution may be produced by dissolving or suspending plasmonic particles in a mobile phase. Flowing the plasmonic particles solution through the immobile phase may include injecting the plasmonic particles solution into the immobile phase, and then flushing the plasmonic particles solution through the immobile phase.

Plasmonic particles of the present invention may be silver particles, gold particles, copper particles, or combinations thereof. The plasmonic particle may be a nanoshell material with a dielectric core surrounded by a shell, where the shell may be comprised of gold, silver, or copper. The plasmonic particle may have a size in the range of approximately 0.5 nm to approximately 200 nm.

In some embodiments, the mobile phase comprises hydrocarbons. In some embodiments, the immobile phase is a subterranean formation. In some embodiments, the immobile phase comprises at least one of sands, sandstones, carbonate rocks, shales, micas, aluminates, silicates, clays, or combinations thereof. In some embodiments, the immobile phase is packed in a column. Other embodiments of the present invention pertain to apparatus for analyzing the transport of plasmonic particles through a mineral formation.

BRIEF DESCRIPTION OF THE FIGURES

FIG. 3A is a schematic of a functionalized nanoparticle, where the nanoparticle is functionalized on its surface with functional groups X. FIG. 3B shows a schematic representation of a core shell nanoparticle with a noble metal shell and a dielectric core.

DETAILED DESCRIPTION

Figure 1:
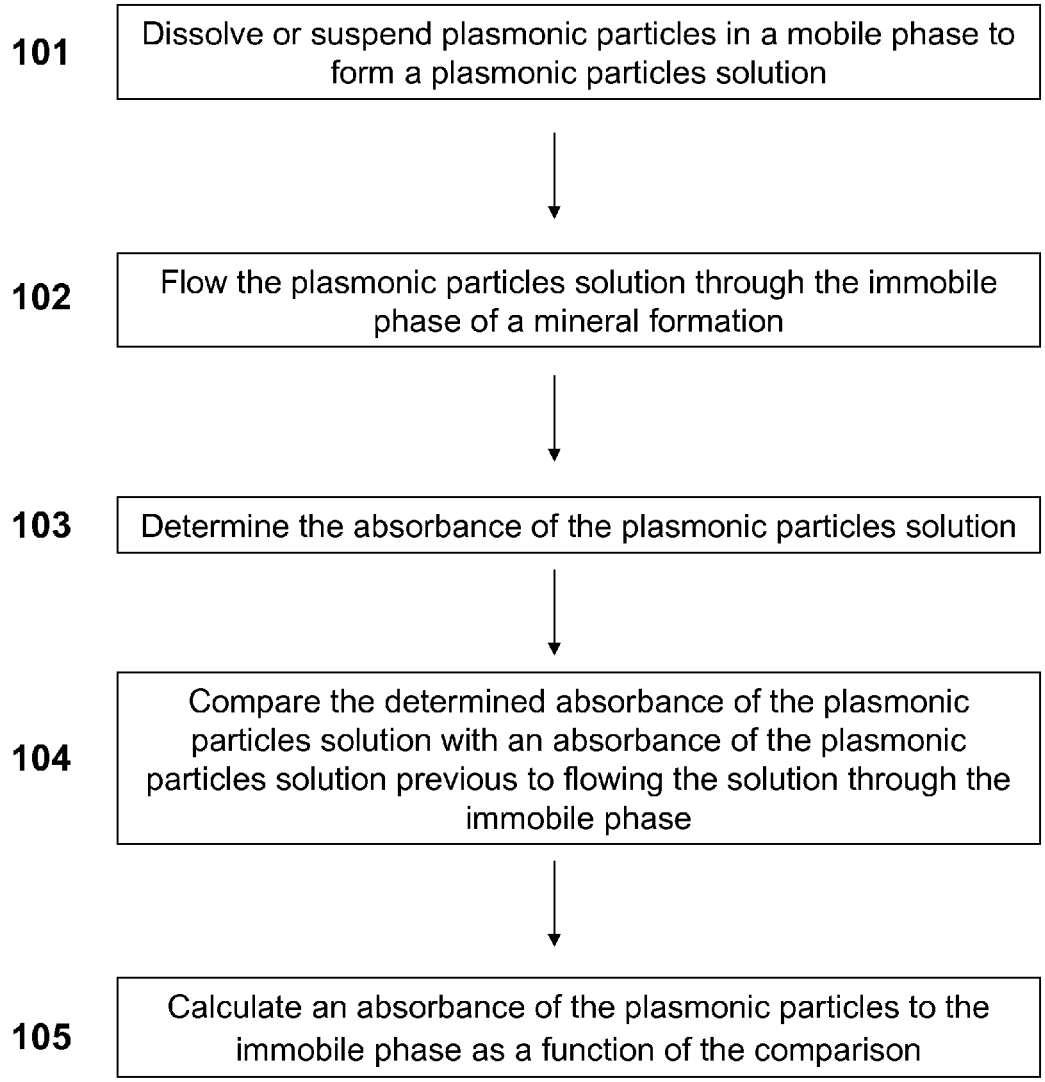
FIG. 1 is a flow diagram illustrating a method of analyzing a transport of plasmonic particles through a mineral formation, in accordance with various embodiments of the present invention.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "particle," "element," and "component" encompass particles, elements, and components, respectively, comprising one unit and particles, elements, and components that comprise more than one unit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

In order to maximize the recovery of oil and gas from subterranean formations and reservoirs, information on the flow characteristics and porosity of the rocks within the reservoir may be obtained. For instance, information on the permeability of a reservoir can be used to determine whether hydraulic fracturing and water flooding is needed, or if they have been successfully implemented.

Methods have been described for characterizing fractured formation properties. For example, Nguyen et al. (U.S. Patent App. Pub. No. 2005/0274510A1) describes the use of a conductive polymer and/or conductive filler phase in a polymer-coated proppant to determine these parameters via an electric field based remote sensing procedure. In another example, Ayoub et al. (U.S. Pat. No. 7,083,993 B2) makes use of either active or passive devices to characterize the fracture parameters. Likewise, McCarthy et al. (US Pat. App. Pub. No. 2006/0102345A1) describes a proppant tracking and fracture zone characterization material.

Additional reservoir characterization methodologies generally include determining reservoir architecture, establishing fluid-flow trends, constructing a reservoir model, and identifying reserve growth potential. Such goals have generally been accomplished using techniques such as seismic measurements and NMR well logging. However, these methods have limitations that necessitate the development of new methods.

For instance, the low porosity and permeability of many oil or gas reservoirs (even after hydraulic fracturing) means that any sensor or tracer material needs a size sufficiently small to allow for its transport through the rock formation. As such, nanoparticles represent a potential sensor material. In particular, the special electrical and magnetic properties of certain nanomaterials make them well suited for use as injected sensors and contrast agents.

One of the issues with measuring the transport of nanoparticles proposed as sensors is that their absorbance is typically weak. For instance, the absorbance peak for iron oxide based particles is very weak, thereby leading to poor data acquisition and spurious results. Thus, much higher concentrations of nanoparticles may be required to obtain valuable measurements. However, such concentrations may interfere with various downhole operations in various reservoirs and subterranean formations.

Referring to FIG. 1, embodiments of the present invention analyze the transport of plasmonic particles through mineral formations that contain an immobile phase. In step 101, plasmonic particles are mixed (e.g., dissolved and/or suspended) in a mobile phase to form a plasmonic particles solution. In step 102, the plasmonic particles solution is caused to flow through an immobile phase, such as a mineral formation, a sample core from a mineral formation, or a simulation of a mineral formation. In step 103, an absorbance of the plasmonic particles solution is determined subsequent to flowing the plasmonic particles solution through the immobile phase. In step 104, the determined absorbance of the plasmonic particles solution is compared with an absorbance of the plasmonic particles solution determined previous to flowing the plasmonic particles solution through the immobile phase. In step 105, an absorbance of the plasmonic particles to the immobile phase is determined as a function of the comparison.

Figure 2:
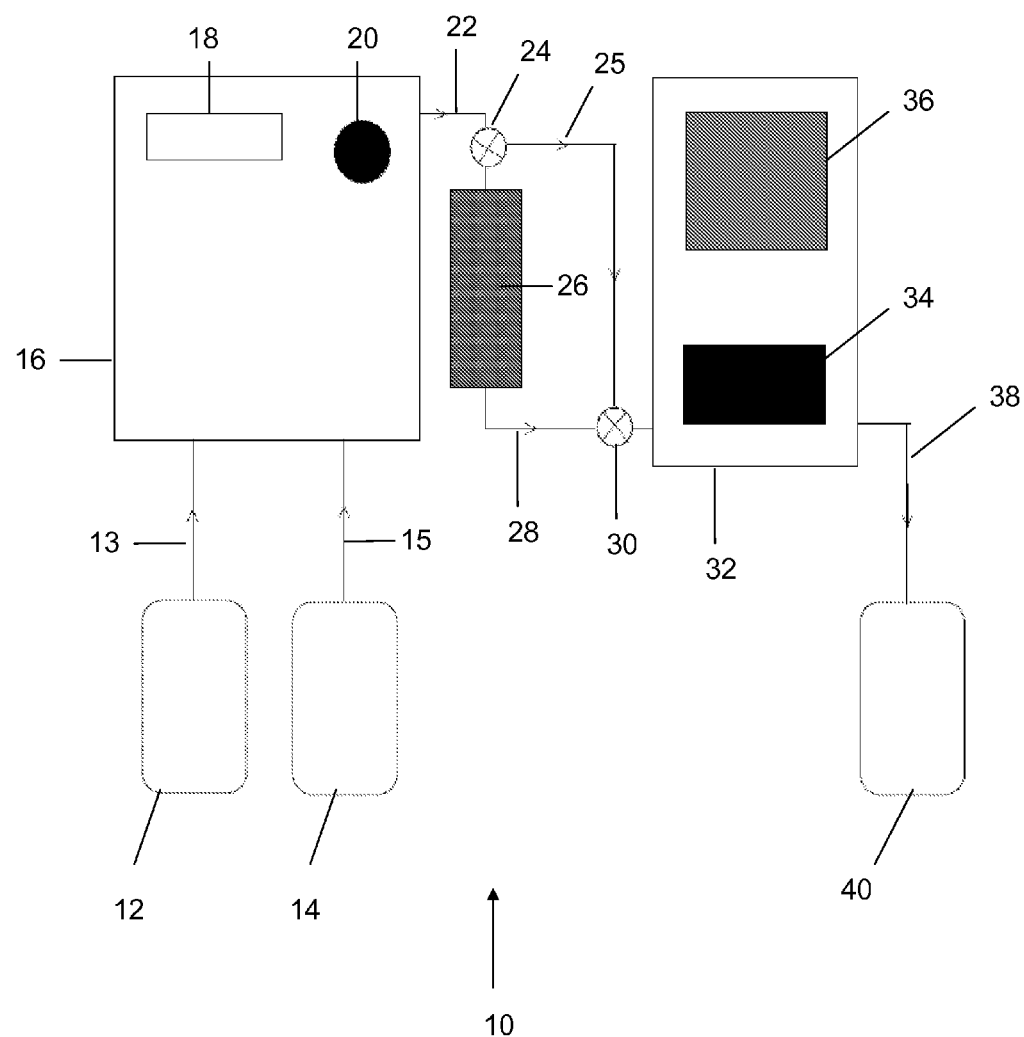
FIG. 2 shows a schematic diagram of an apparatus for analyzing a transport of plasmonic particles through a mineral formation, in accordance with various embodiments of the present invention.

Various apparatus may be used to analyze the transport of plasmonic particles through mineral formations. An apparatus that may be used to analyze the transport of plasmonic particles through an immobile phase is shown in FIG. 2 as apparatus 10. In this embodiment, apparatus 10 includes a mobile phase container 12, plasmonic particle container 14, consolidating container 16, immobile phase column 26, housing 32 containing UV detector 34 and computer 36, and waste container 40.

Plasmonic particle container 14 contains plasmonic particles, as described in more detail herein. The plasmonic particles may be suspended in various solvents and/or solutions at various concentrations.

Mobile phase container 12 contains a mobile phase, which may be any stock solution that can solvate or suspend plasmonic particles under investigation. As discussed in more detail below, the mobile phase may also be used to calibrate UV detector 34.

Mobile phase container 12 and plasmonic particle container 14 may be connected to consolidating container 16 via tubings 13 and 15, respectively. Consolidating container 16 may also contain flow rate meter 18 and flow rate adjuster 20. In some embodiments, flow rate meter 18 and flow rate adjuster 20 are electronic input devices that allow control of injections from mobile phase container 12 and plasmonic particle 14 at different ratios, times, and flow rates.

In some embodiments, consolidating container 16 may be a modified Combi Flash gear pump (Serial Number 204J20171, Combi Flash Companion). In some embodiments, the Combi Flash gear pump's dispensing arm (usually used to dispense into a tray containing test tubes) is modified such that the tube has been disconnected from the dispensing arm and connected to housing 32 and immobile phase column 26. In some embodiments, such connections may be achieved via a plastic luer to a tygon tube that flows directly into housing 32 or immobile phase column 26.

In some embodiments, consolidating container 16 may be connected to immobile phase column 26 through tubing 22. As discussed in more detail herein, immobile phase column 26 may be any column that is packed with an immobile phase. In some embodiments, immobile phase column 26 may be a Redisep column that is approximately 2 cm in diameter and approximately 6.5 cm in length. The immobile phase column may be made of various materials, including inert materials such as nylons, glasses, plastics, and/or metals. Additional suitable immobile phase columns may also be envisioned by persons of ordinary skill in the art.

The immobile phase may contain any material that is typical of that found in a subterranean formation (e.g., any mineral formation component, such as minerals, rocks, sand, and the like, such as found in an oil or gas reservoir). The immobile phase may contain a proppant material. The immobile phase may be configured to simulate the mineral formations of a subterranean formation (e.g., an oil, gas, or water reservoir) under investigation. The immobile phase may contain a core obtained from a well bore.

As also shown in FIG. 2, immobile phase column 26 may be connected to housing 32 through tubing 28. In turn, housing 32 may be connected to waste container 40 through tubing 38.

Housing 32 may contain UV detector 34 and computer 36. UV detector 34 may be any suitable UV detector, such as a UV spectrophotometer (e.g., a commercially available Agilent 8453 UV-Visible spectrophotometer, which uses a photodiode array (PDA)). Other suitable UV detectors may also be envisioned by persons of ordinary skill in the art.

Computer 36 may utilize various software and/or hardware for detecting or analyzing the flow of nanoparticles. The software in computer 36 may be commercially available Agilent ChemStation (kinetics version). The use of other software may also be envisioned by persons of ordinary skill in the art.

In an operation according to embodiments of the present invention, the mobile phase in container 12 and the plasmonic particles in container 14 are released into consolidating container 16 through tubings 13 and 15, respectively. This results in the dissolving and/or suspending of the plasmonic particles in the mobile phase to form plasmonic particles solution (see step 101 of FIG. 1). The plasma particle solution is then caused to flow through immobile phase column 26 via tubings 22 and 28 (see step 102 of FIG. 1). This flow may be controlled by valves 24 and/or 30. The flow may also be controlled by various pumps and actuators that are well known to persons of ordinary skill in the art.

Plasmonic particles may absorb to contents in immobile phase column 26 as the plasmonic particles solution is flowing therethrough. Thereafter, the plasmonic particles solution is caused to flow into housing 32. UV detector 34 in housing 32 may then be used to determine the absorbance of the plasmonic particles solution after it has passed through the immobile phase column 26 (see step 103 of FIG. 1). Alternatively, the plasmonic particles solution may be injected into a subterranean formation through a well bore (or a sample core taken from a well bore) and then retrieved (for example, via a second well bore in a vicinity of the first well bore in which the particles were injected). The retrieved plasmonic particles solution is then inserted into consolidating container 16, and valves 24 and 30 directed such that the retrieved plasmonic particles solution in container 16 flows into housing 32 through tubings 22 and 25. UV detector 34 is then used to determine the absorbance of the retrieved plasmonic particles solution, which is then compared to the absorbance of the plasmonic particles solution determined before the injection of the solution into the subterranean formation.

As a pre-calibration step, the aforementioned process may also be conducted such that the plasmonic particles solution in consolidating container 16 bypasses immobile phase column 26. For instance, valves 24 and 30 may be directed such that the plasmonic particles solution in container 16 flows into housing 32 through tubings 22 and 25. UV detector 34 may then used to determine the absorbance of the plasmonic particles solution that did not pass through immobile phase column 26 (see step 104 of FIG. 1). An output of UV detector 34 may be a set of absorbance data in raw format and/or in the form of a plot on a graph (e.g., FIGS. 11 and 15-36), which may be inputted into computer 36.

The absorbance of plasmonic particles onto the immobile phase may then be determined based on the comparison of the absorbance of the plasmonic particles solution that passed through the immobile phase column with the absorbance of the plasmonic particles solution that bypassed the immobile phase column (see step 105 of FIG. 1). Such a determination may be aided by the utilization of computer 36 with the aid of a software program.

As a washing step, the aforementioned process may be repeated by flowing the mobile phase through the immobile phase column until the absorbance returns to its original absorbance.

Figure 36:
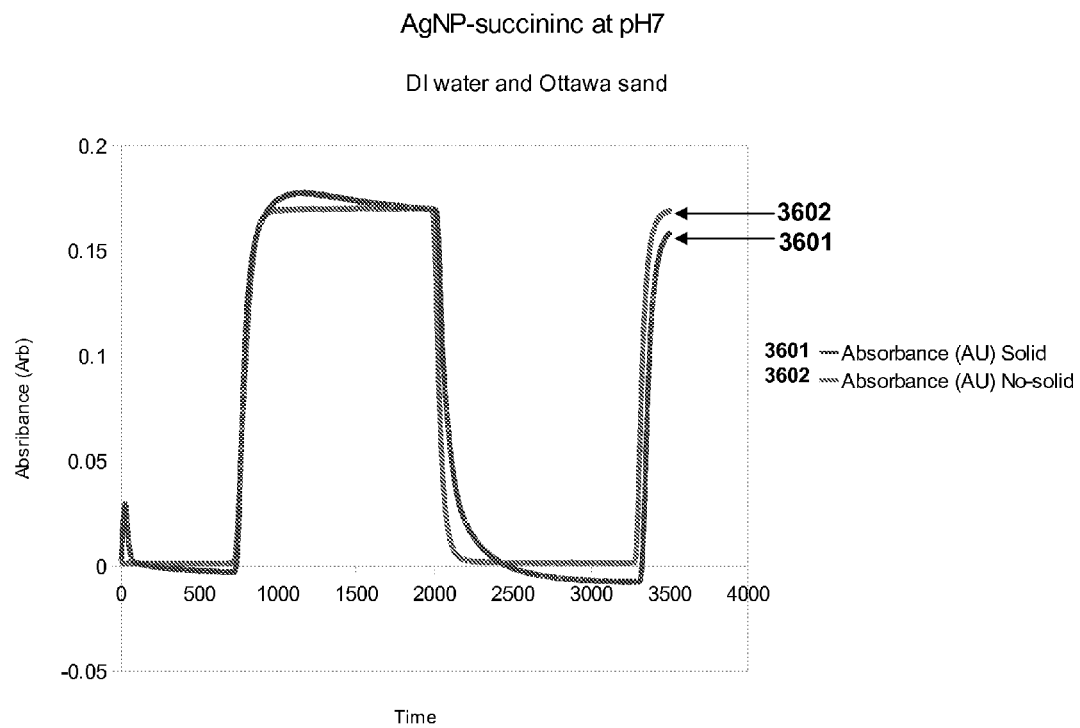
FIG. 36 shows a comparative absorbance curve as a function of elution time for silver nanoparticles capped with mercaptosuccinic acid that were passed through a minimum volume tube, as illustrated in FIG. 2 and described in Example 2.

Referring to FIG. 36, line 3601 is a plot of an absorbance curve of plasmonic particles that were passed through immobile phase column 26. Line 3602 is a plot of an absorbance curve of the plasmonic particles that bypassed immobile phase column 26. The difference in trends between these two curves may be used to determine how the plasmonic particles deposit onto the contents in immobile phase column 26 (e.g., the "stickiness" of the plasmonic particles to the immobile phase).

For instance, the absorbance of line 3601 at one or more particular times may be compared to the absorbance of line 3602 at the same particular times. The absorbance of the plasmonic particles to the contents of immobile phase column 26 may then be calculated at those times as a function of the comparison.

In some embodiments, the comparison may involve calculating the difference in absorbance between line 3601 and line 3602 at one or more particular times. In some embodiments, the comparison may involve determining the difference in the calculated concentrations of plasmonic particles in lines 3601 and 3602 at one or more particular times. In some embodiments, the comparison may involve calculating the sticking coefficient of the plasmonic particles to immobile phase column 26, as discussed in more detail below. FIG. 36 is also further discussed below.

Plasmonic Particles

Embodiments of the present invention may utilize various plasmonic particles. Plasmonic particles generally refer to particles with plasmonic properties, such as Surface Plasmon Resonance (SPR), and the properties discussed in more detail below.

By way of information, a plasmon is a quantum of plasma oscillation. The plasmon is a quasi-particle resulting from the quantization of plasma oscillations, just as photons and phonons are quantizations of light and mechanical vibrations, respectively. Thus, plasmons are collective oscillations of the free electron gas density, for example, at optical frequencies, such as in the ultraviolet range (UV). The UV wavelength is particularly resonant with the oscillating free electron gas of noble metal particles in the nanoscale range.

Examples of plasmonic particles include silver particles, gold particles, copper particles, and combinations thereof. As set forth in more detail below, such plasmonic particles may have various shapes, sizes, and functional groups.

By way of further information, and without being bound by theory, small particles (e.g., particles smaller than the wavelength of light) have an incident electromagnetic field (EMF) that is generally uniform across the particle. Such EMF uniformity causes surface electrons on the particles to move in phase. In addition, incident EMF radiation accelerates these electrons and causes them to circulate across the particle surface. The formation of quasi-dipoles results from the temporary charge differences that exist across the particle. In addition, the electrons oscillate periodically across the particle in resonance with the incident radiation.

The dipoles occur when electrons from the surface are drawn to one end of the particle, thereby leaving a temporary positive charge on the opposite side. As light passes over the particle, the electrons are drawn to the other end of the particle. This process can continue back and forth across the particle surface.

The presence of a restoring force results from the polarization of the light. This system of electrons sloshing back and forth is known as plasmonic, and the plasmon frequency is found to have discrete resonance frequencies with the incident light. The incident light resonates with the surface electrons. The light in turn creates temporary positive charges on the opposite side of the particles that oscillate back and forth. This whole process is known as Surface Plasmon Resonance (SPR).

SPR typically results in a sharp absorbance peak with a wavelength that depends on the dielectric function of the material and the solvent. Because the SPR of a nanoparticle is very discrete, it can be deliberately created in one part of the spectrum or another.

For instance, silver nanoparticles with a mean diameter of 20 nm have a well-defined peak at a $\lambda_{abs}^{np}$ of 400 nm. In addition, the UV-vis spectrum for silver nanoparticles is unique on how it spans the visible part of the spectrum, and how a size increase can lead to a shift in the absorbance peak. See, e.g., Y. Zhao et al., *Spectrochimica Acta Part A*, 2006, 65, 1003.

Other metals such as copper and gold have also been found to exhibit a strong SPR effect in the UV and visible spectrums. In addition, the tuning of the SPR wavelength can be tailored by altering the aspect ratio of the materials.

Iron-oxide nanoparticles have been directly measured to analyze the transport of nanoparticles. However, such methods present various limitations, including measurement accuracy and detection at low concentrations. In particular, iron-oxide nanoparticles generally have a weak tendency toward surface plasmon resonance in the UV-visible spectral range. In contrast, iron oxides generally exhibit a peak absorbance of around 370 nm. Since this peak absorbance is close to the cut off frequency of a UV-visible spectrometer (i.e., 200 nm), the iron-oxide nanoparticle surface plasmon resonance peak is often not fully presented in the spectra.

Furthermore, the absorbance peak for iron oxide is very weak, thereby leading to poor data acquisition and spurious results that prevent systems from reaching a stable and continuous plateau for determining a baseline value. In fact, for iron oxide, the absorbance usually does not reach a plateau and instead continues to increase or decrease sporadically, even under controlled conditions.

Figure 4:
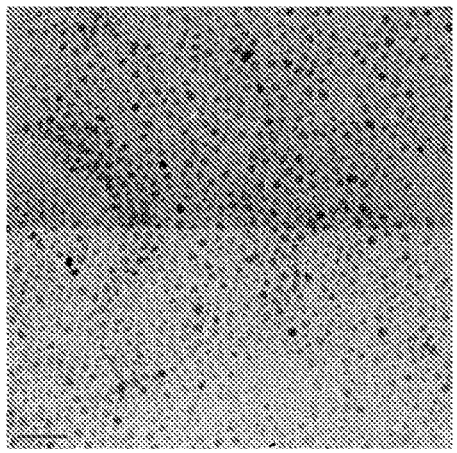
FIG. 4 is a Transmission Electron Micrograph (TEM) of 10 nm $Fe_2O_3$ glutamic acid capped ferrite nanoparticles.

FIGS. 16A, 16B, and 16C show examples of poor UV detection, baseline, and plateauing of injections of 100% $Fe_2O_3$ nanoparticles capped with glutamic acid solutions at pH 7 pumped directly through a UV detector, at 10 mL min$^{-1}$. FIG. 4 is a Transmission Electron Micrograph (TEM) of 10 nm $Fe_2O_3$ glutamic acid capped ferrite nanoparticles. The Agilent software was programmed for a 1 cm cell. Absorbance for the UV was programmed for 340 nm absorbance and for 12,600 seconds, data points were taken every 0.5 seconds. HPLC grade Chromosolve $H_2O$ was used as stock solution. The gear pump software was programmed to inject 40 mL of only 100% stock solution. Only 100% nanoparticles were then injected for 20 mins. This procedure was repeated 3 times. Then, 100% stock solution was washed through the UV detector for 30 mins. to remove unbound nanoparticles.

Figure 5:
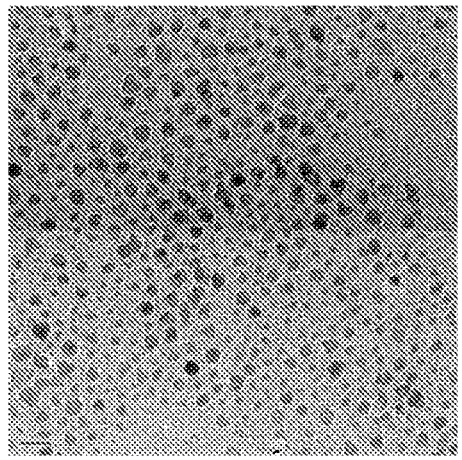
FIG. 5 is a TEM of 10 nm $Fe_2O_3$ lysine capped ferrite nanoparticles.

FIGS. 17A, 17B and 17C also show examples of poor UV detection, baseline, and plateauing of injections of 100% $Fe_2O_3$ nanoparticles capped with lysine solution at pH 7 pumped directly through a UV detector, at 10 mL min$^{-1}$. Likewise, FIG. 5 is a TEM of 10 nm $Fe_2O_3$ glutamic acid capped ferrite nanoparticles. The same experimental protocols described for FIGS. 16 and 4 were also used for these experiments.

Figure 6:
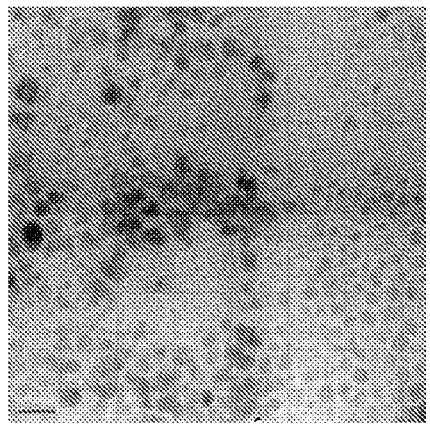
FIG. 6 is a TEM of 15 nm $Fe_2O_3$ cysteic acid capped ferrite nanoparticles.

FIGS. 18A, 18B and 18C show examples of poor UV detection, baseline, and plateauing of injections of 100% $Fe_2O_3$ nanoparticles capped with cysteic acid solution at pH 7 pumped directly through a UV detector, at 10 mL s$^{-1}$. Likewise, FIG. 6 is a TEM of 10 nm $Fe_2O_3$ cysteic acid capped ferrite nanoparticles. The same experimental protocols described for FIGS. 16 and 4 were also used for these experiments.

Figure 19:
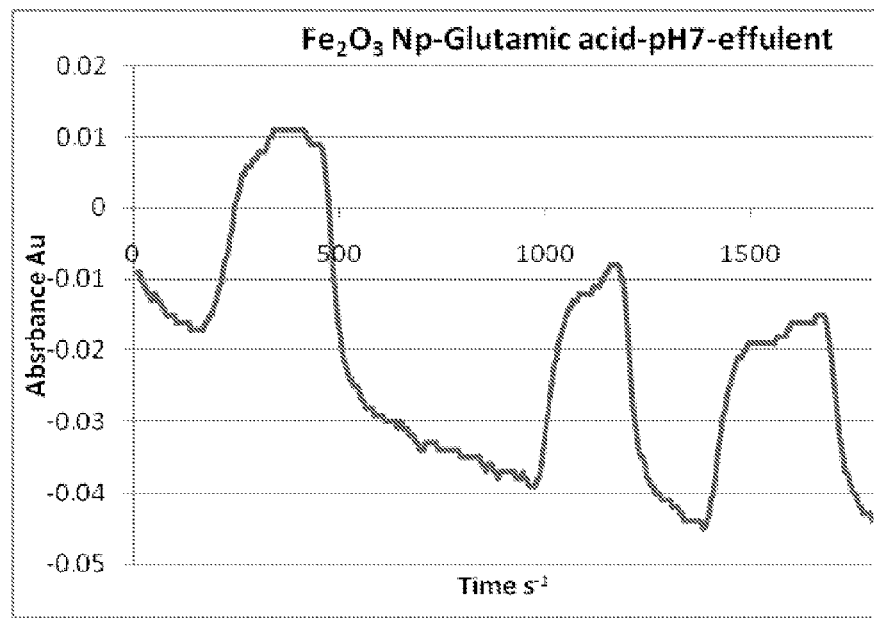
FIG. 19 shows a UV absorbance spectrum of injections of 100% $Fe_2O_3$ nanoparticles capped with glutamic acid solution at pH 7. The samples were passed through a column containing Ottawa sand, as illustrated in FIG. 2 and described in Example 2.

FIG. 19 shows an example of poor UV detection, no stable baseline, and no plateauing of injections of 100% $Fe_2O_3$ nanoparticles capped with glutamic acid solution at pH 7 pumped through a 6.5 cm length 2.0 cm diameter Redisep column containing Ottowa sand of known size and porosity. The same experimental protocols described for FIG. 16 were also used for this experiment.

Figure 20:
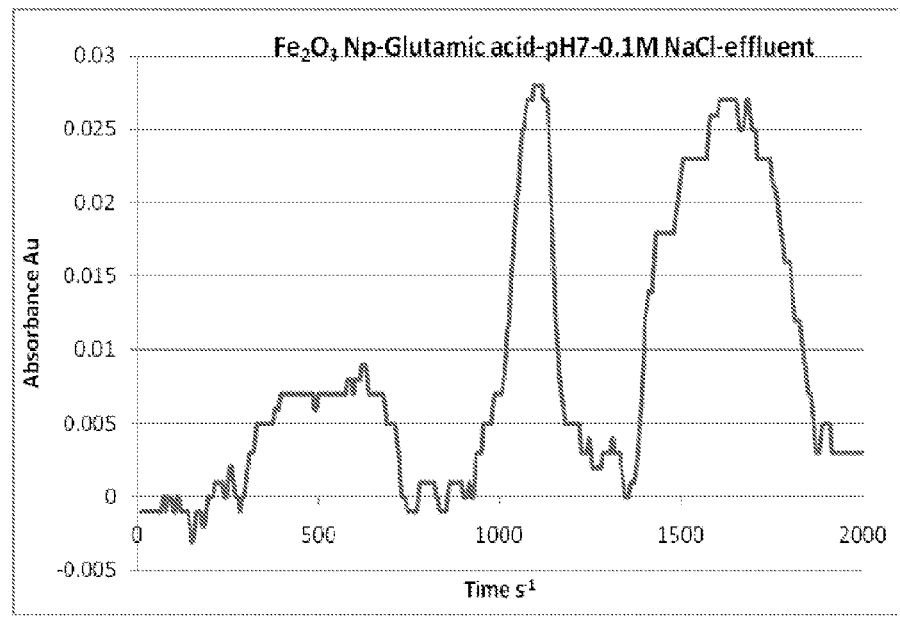
FIG. 20 shows a UV absorbance spectrum of injections of 100% $Fe_2O_3$ nanoparticles capped with glutamic acid solution at pH 7 containing 0.1 M NaCl. The samples were passed through a column containing Ottawa sand, as illustrated in FIG. 2 and described in Example 2.

FIG. 20 shows an example of poor UV detection, no stable baseline, and no plateauing of injections of 100% $Fe_2O_3$ nanoparticles capped with glutamic acid solution at pH 7, 0.1 M NaCl pumped through a 6.5 cm length 2.0 cm diameter Redisep column containing Ottowa sand of known size and porosity. The same experimental protocols described for FIG. 16 were also used for this experiment.

Figure 21:
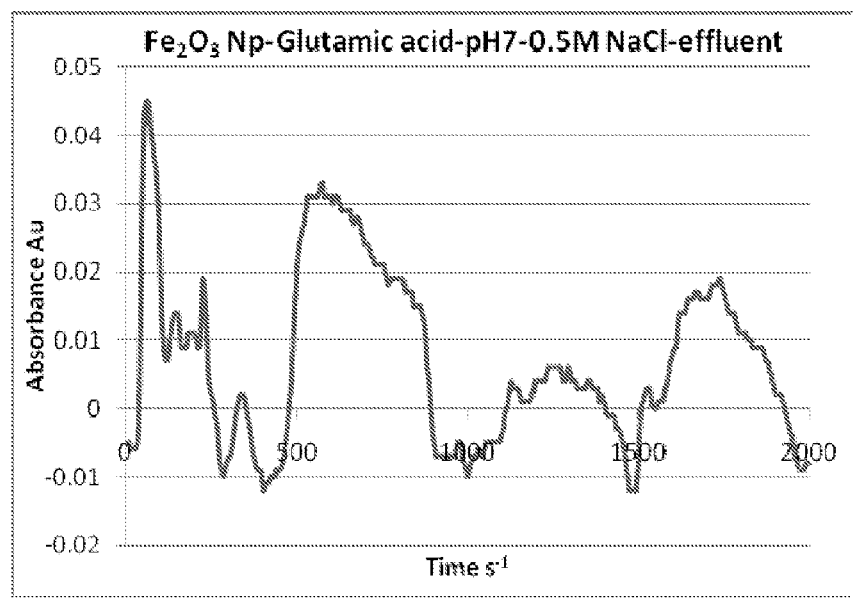
FIG. 21 shows a UV absorbance spectrum of injections of 100% $Fe_2O_3$ nanoparticles capped with glutamic acid solution at pH 7 containing 0.5 M NaCl. The samples were passed through a column containing Ottawa sand, as illustrated in FIG. 2 and described in Example 2.

FIG. 21 shows an example of poor UV detection, no stable baseline, and no plateauing of injections of 100% $Fe_2O_3$ nanoparticles capped with glutamic acid solution at pH 7, 0.5 M NaCl pumped through a 6.5 cm length 2.0 cm diameter Redisep column containing Ottowa sand of known size and porosity. The same experimental protocols described for FIG. 16 were also used for this experiment.

Figure 22:
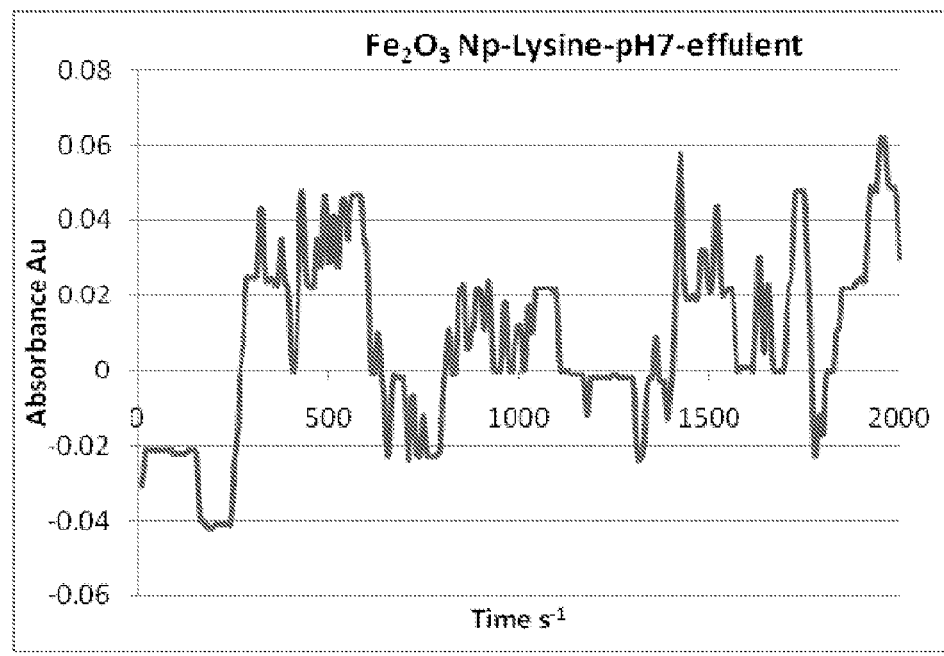
FIG. 22 shows a UV absorbance spectrum of injections of 100% $Fe_2O_3$ nanoparticles capped with lysine at pH 7. The samples were passed through a column containing Ottawa sand, as illustrated in FIG. 2 and described in Example 2.

FIG. 22 shows an example of poor UV detection, no stable baseline, and no plateauing of injections of 100% $Fe_2O_3$ nanoparticles capped with lysine solution at pH 7 pumped through a 6.5 cm length 2.0 cm diameter Redisep column containing Ottowa sand of known size and porosity. The same experimental protocols described for FIG. 16 were also used for this experiment.

Figure 23:
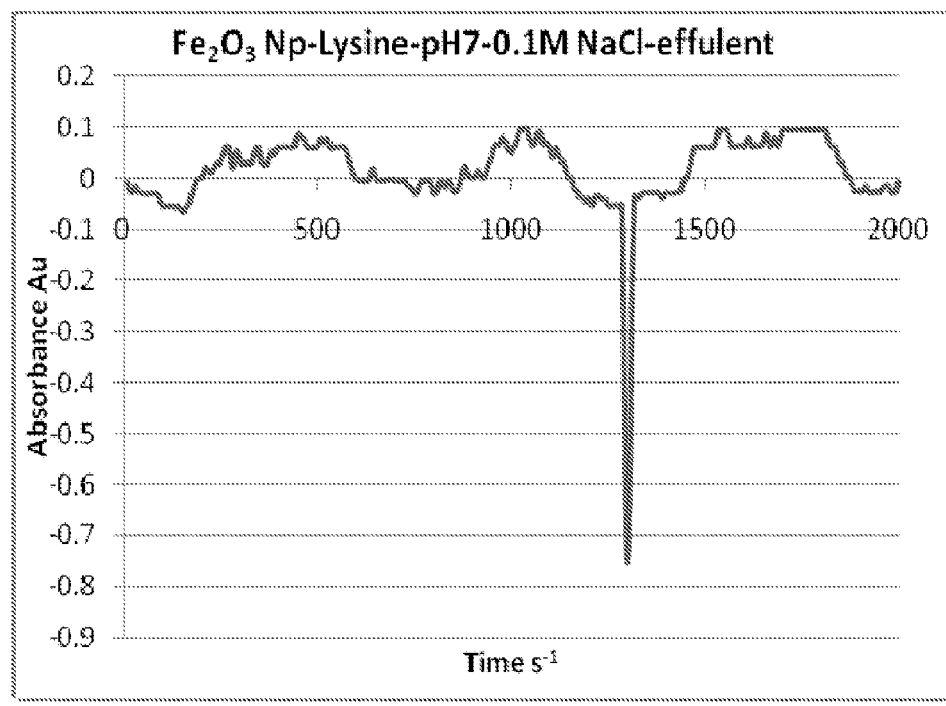
FIG. 23 shows a UV absorbance spectrum of injections of 100% $Fe_2O_3$ nanoparticles capped with a lysine solution at pH 7 containing 0.1 M NaCl. The samples were passed through a column containing Ottawa sand, as illustrated in FIG. 2 and described in Example 2.

FIG. 23 shows an example of poor UV detection, no stable baseline, and no plateauing of injections of 100% $Fe_2O_3$ nanoparticles capped with lysine solution at pH 7, 0.1 M NaCl pumped through a 6.5 cm length 2.0 cm diameter Redisep column containing Ottowa sand of known size and porosity. The same experimental protocols described for FIG. 16 were also used for this experiment.

Figure 24:
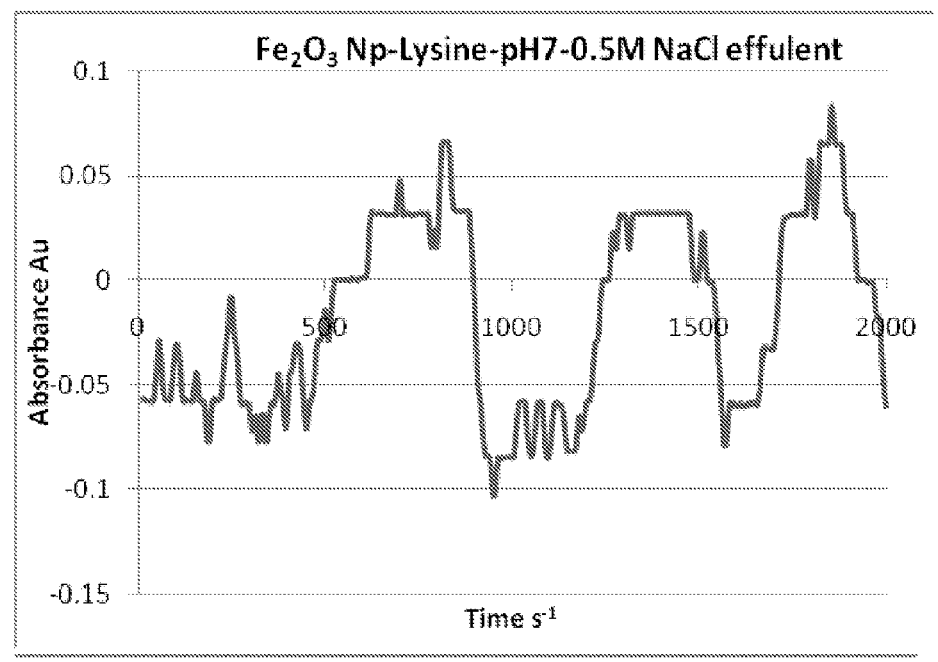
FIG. 24 shows a UV absorbance spectrum of injections of 100% $Fe_2O_3$ nanoparticles capped with a lysine solution at pH 7 containing 0.5 M NaCl. The samples were passed through a column containing Ottawa sand, as illustrated in FIG. 2 and described in Example 2.

FIG. 24 shows an example of poor UV detection, no stable baseline, and no plateauing of injections of 100% $Fe_2O_3$ nanoparticles capped with lysine solution at pH 7, 0.5 M NaCl pumped through a 6.5 cm length 2.0 cm diameter Redisep column containing Ottowa sand of known size and porosity. The same experimental protocols described for FIG. 16 were also used for this experiment.

Figure 25:
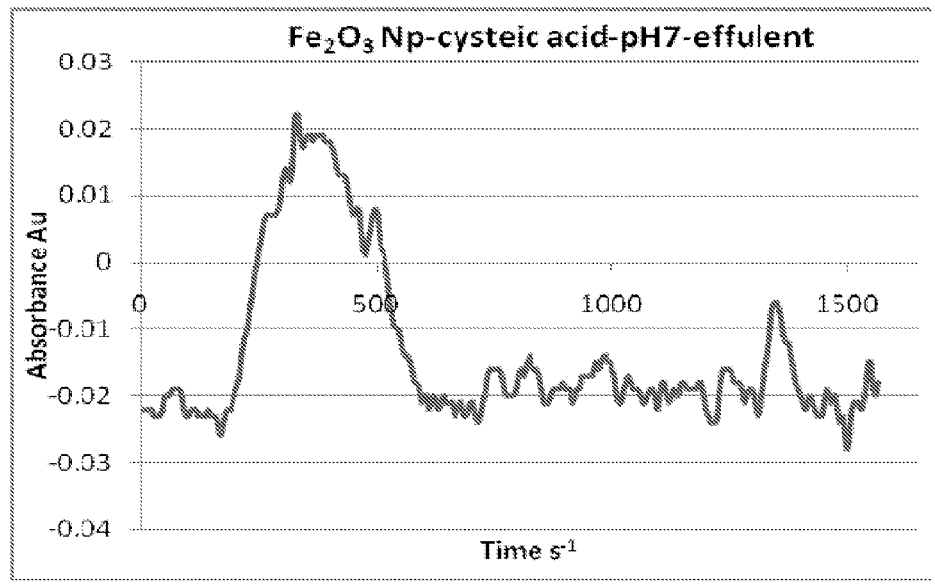
FIG. 25 shows a UV absorbance spectrum of injections of 100% $Fe_2O_3$ nanoparticles capped with cysteic acid solution at pH 7. The samples were pumped directly through a UV detector, as illustrated in FIG. 2 and described in Example 2.

FIG. 25 shows an example of poor UV detection, baseline, and plateauing of injections of 100% $Fe_2O_3$ nanoparticles capped with cysteic acid solution at pH 7 pumped directly through a UV detector, at 10 mL s$^{-1}$. The same experimental protocols described for FIG. 16 were also used for this experiment.

Figure 26:
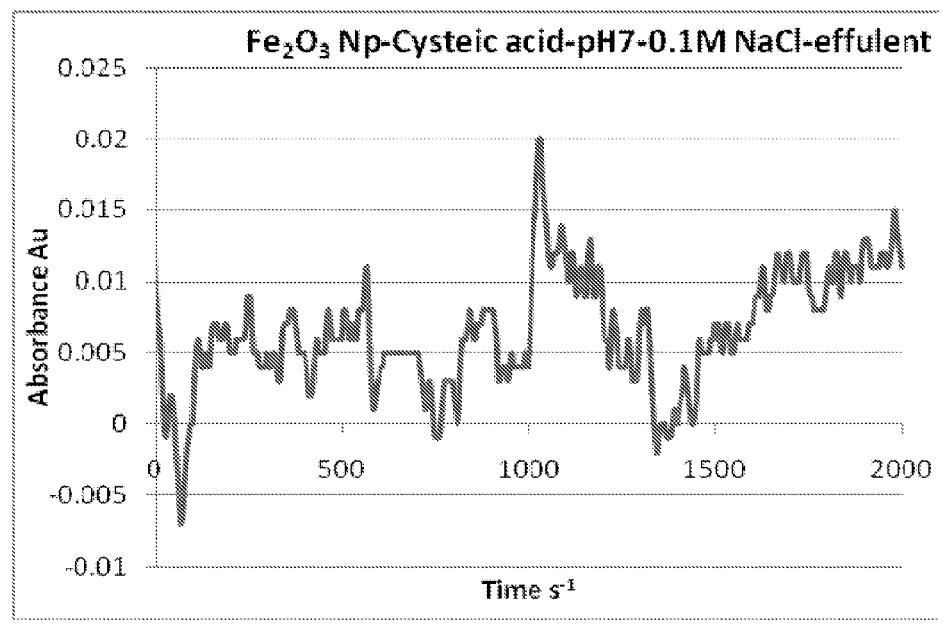
FIG. 26 shows a UV absorbance spectrum of injections of 100% $Fe_2O_3$ nanoparticles capped with cysteic acid solution at pH 7 containing 0.1 M NaCl. The samples were passed through a column containing Ottawa sand, as illustrated in FIG. 2 and described in Example 2.

FIG. 26 shows an example of poor UV detection, baseline, and plateauing of injections of 100% $Fe_2O_3$ nanoparticles capped with cysteic acid solution at pH 7, 0.1 M NaCl pumped through a 6.5 cm length 2.0 cm diameter Redisep column containing Ottowa sand of known size and porosity. The same experimental protocols described for FIG. 16 were also used for this experiment.

Figure 27:
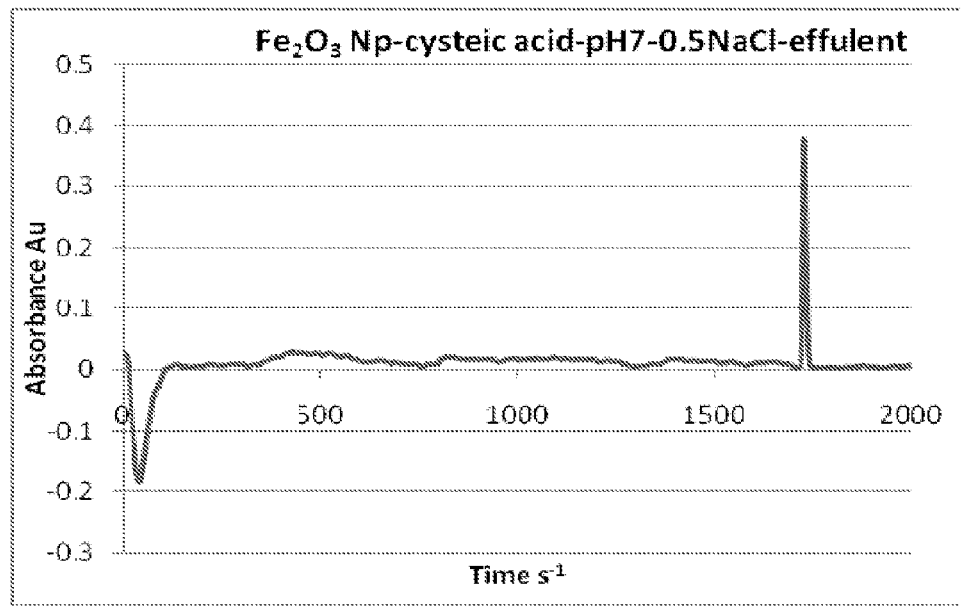
FIG. 27 shows a UV absorbance spectrum of injections of 100% $Fe_2O_3$ nanoparticles capped with cysteic acid solution at pH 7 containing 0.5 M NaCl. The samples were passed through a column containing Ottawa sand, as illustrated in FIG. 2 and described in Example 2.

FIG. 27 shows an example of poor UV detection, baseline, and plateauing of injections of 100% $Fe_2O_3$ nanoparticles capped with cysteic acid solution at pH 7, 0.5 M NaCl pumped through a 6.5 cm length 2.0 cm diameter Redisep column containing Ottowa sand of known size and porosity. The same experimental protocols described for FIG. 16 were also used for this experiment.

Utilizing plasmonic particles provides a more accurate and sensitive analysis of the transport of particles through a mineral formation, even at low concentrations. Without being bound by theory, it is believed that such improvements are due to the efficiency of the plasmonic particle at absorbing UV radiation.

For instance, silver nanoparticles display a very stable and consistent UV-visible absorbance with the peak absorbance occurring within a very narrow range centered at 400 nm. This range is well within the optical detection limits of UV-visible spectrophotometers, thus ensuring that both the leading and the trailing edges of the peaks become visible. When both the leading and trailing edges are present, then it is possible to make an optimal calculation of the Full Width at Half the Maximum (FWHM).

Furthermore, silver nanoparticles have a strong peak absorbance that can be detected at much lower concentrations than that of the iron oxide nanoparticles. In addition, the silver nanoparticles offer larger and more consistent peak absorbance, thereby allowing more accurate detection of nanoparticles at low concentrations.

For instance, in some embodiments, the detection range of plasmonic particles may be between 0.1 mg/L to 5 g/L. In some embodiments, the accuracy of the lower limit may be determined by the accuracy of the UV machine used and could be extended by adaptation of a flow cell and/or photo diode. An increase in the accuracy of the upper detection limits could also be achieved using the same methodologies.

Figure 15:
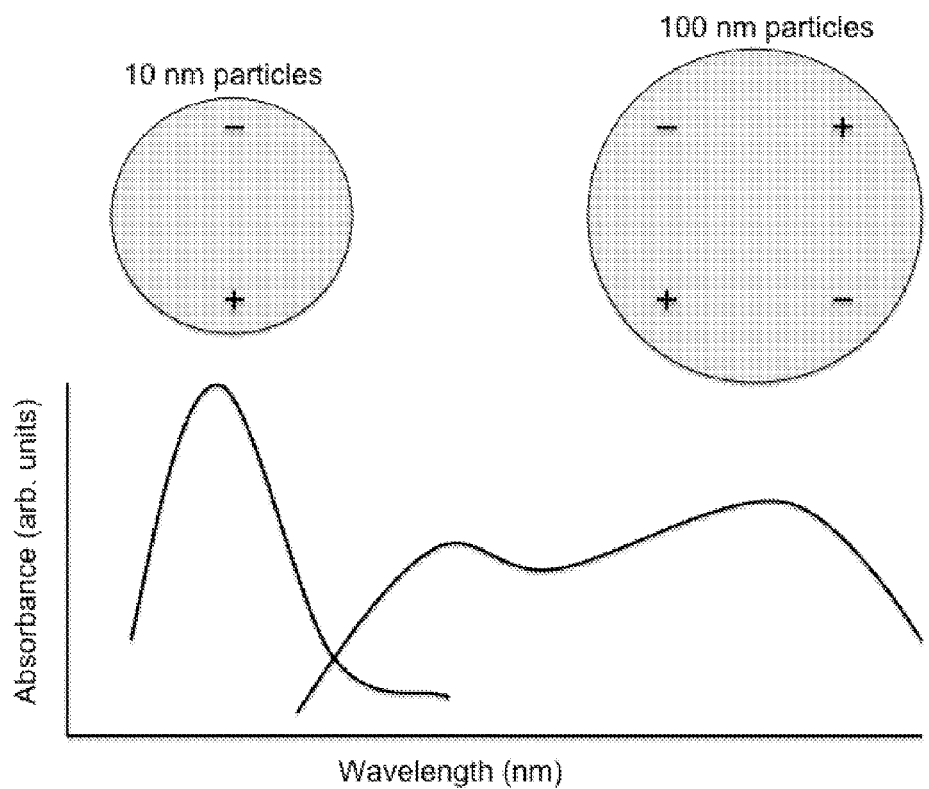
FIG. 15 is an example of a UV absorbance spectrum of plasmonic nanoparticles changing according to the size and shape of the nanoparticles. The diagram shows a comparison of the typical plasmonic response from a plasmonic nanoparticle with an average diameter of approximately 10 nm with the plasmonic response of a nanoparticle with multiple poles.
Figure 16:
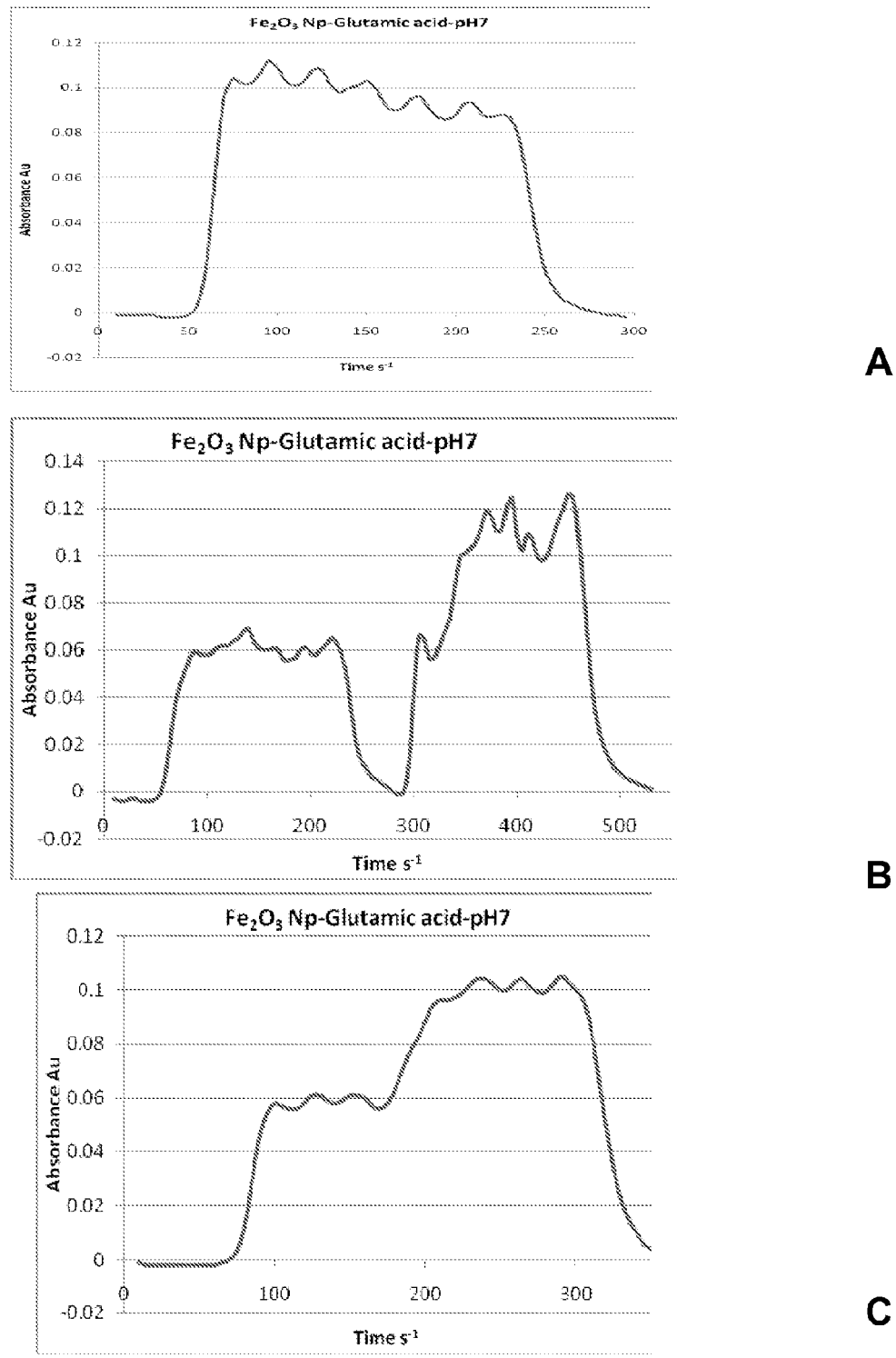
FIG. 16 shows UV absorbance spectra of injections of 100% $Fe_2O_3$ nanoparticles capped with glutamic acid solutions at pH 7. The samples were injected into apparatus 10, as shown in FIG. 2 and described in Example 2. The spectra are shown in FIGS. 16A, 16B and 16C.
Figure 17:
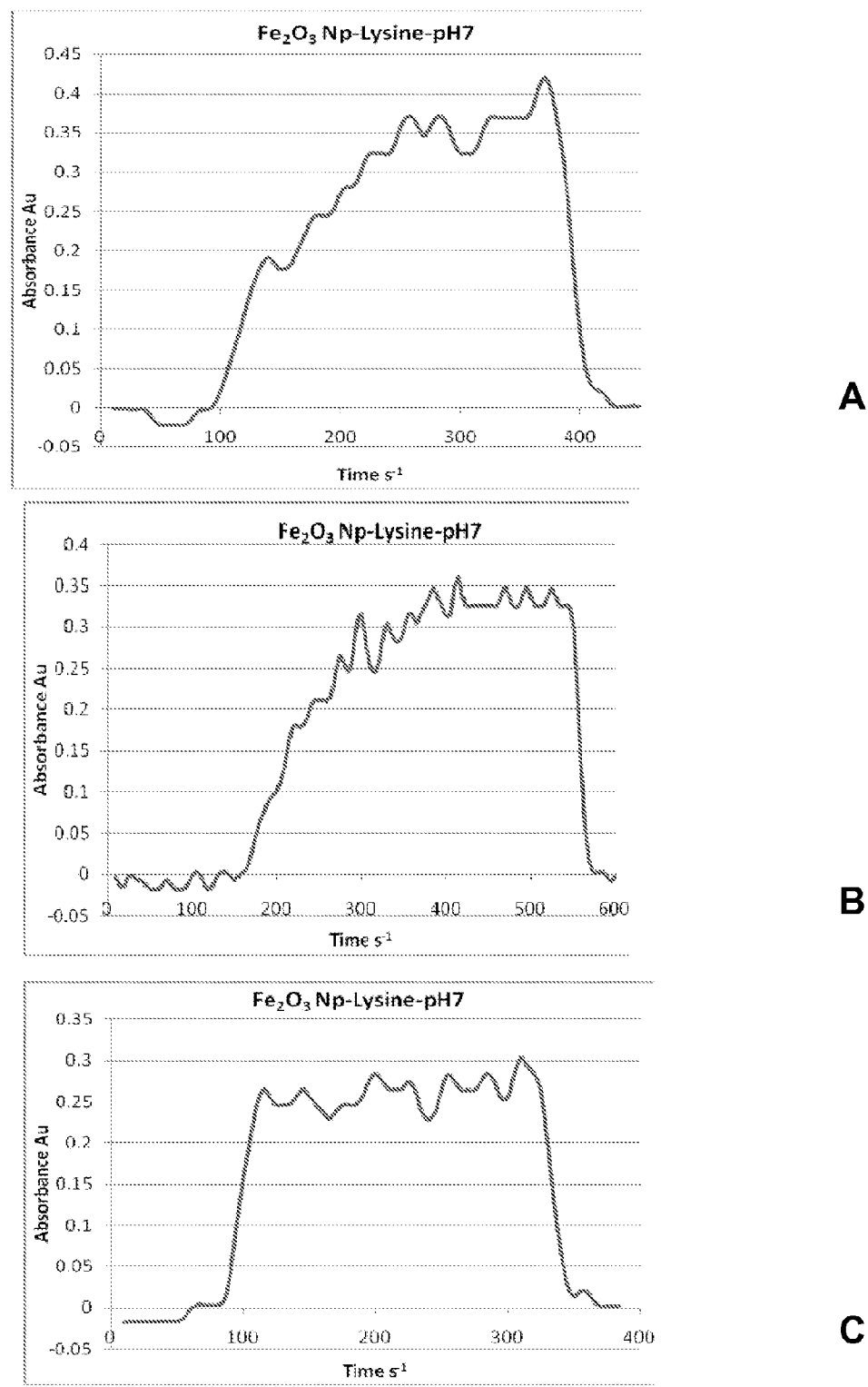
FIG. 17 shows UV absorbance spectra of injections of 100% $Fe_2O_3$ nanoparticles capped with lysine solution at pH 7. The samples were pumped directly through a UV detector of apparatus 10, as shown in FIG. 2 and described in Example 2. The spectra are shown in FIGS. 17A, 17B and 17C.
Figure 18:
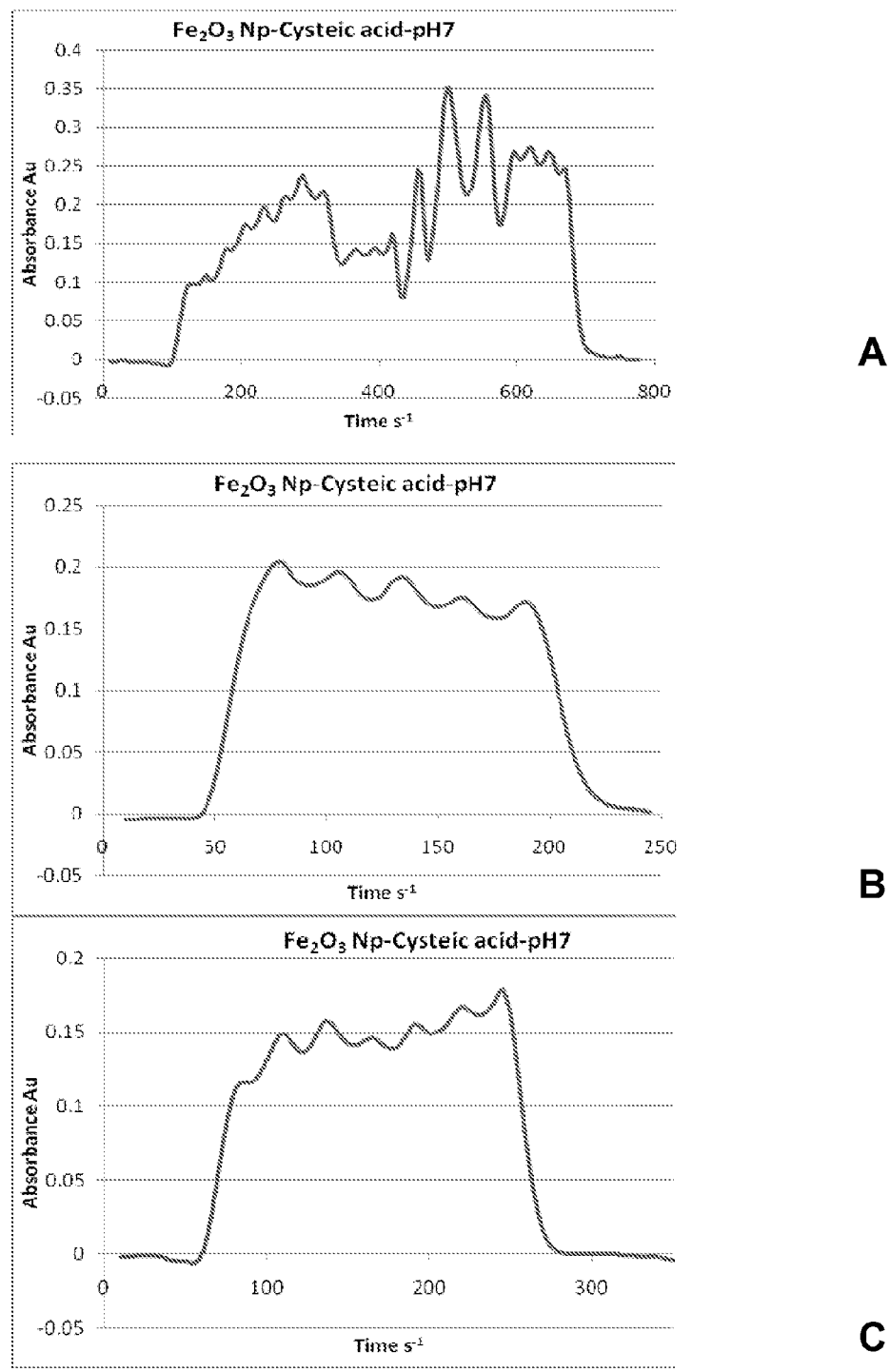
FIG. 18 shows UV absorbance spectra of injections of 100% $Fe_2O_3$ nanoparticles capped with cysteic acid solution at pH 7. The samples were pumped directly through a UV detector of apparatus 10, as shown in FIG. 2 and described in Example 2. The spectra are shown in FIGS. 18A, 18B and 18C.

Moreover, as indicated in FIG. 15, the silver nanoparticle surface plasmon resonance can be tuned according to the size of the nanoparticle. In addition, the size of the nanoparticle can be determined by calculation using the FWHM. See, e.g., C. Okkyoung et al., *Water Research*, 2008, 42, 3066. As set forth in more detail below, the surface functional groups of the silver nanoparticles can also be changed to tailor the stickiness or solubility of the silver nanoparticles in a range of solvents, and under a variety of physical and chemical conditions.

In addition to silver nanoparticles, various other plasmonic particles may be used in embodiments of the present invention. In some embodiments, the plasmonic particles are made of gold and/or copper.

Figure 3:
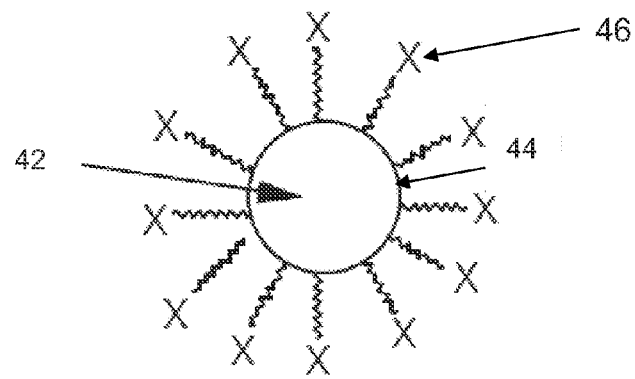
FIG. 3 is a schematic representation of functionalized nanoparticles.
Figure 3:
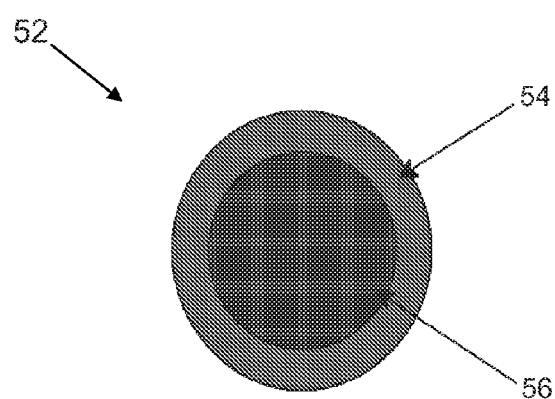

In some embodiments, the plasmonic particle is a nanoshell material that comprises a dielectric core surrounded by a shell. In such embodiments, the shell may comprise at least one of gold, silver, or copper. An exemplary diagram of such a nanoparticle is shown in FIG. 3B as nanoparticle 52, which has a dielectric core 56 and shell 54. In some embodiments, by using such a nanoparticle, the absorbance of UV light can be absorbed at different wavelengths as the free electron gas contained in the shell forms a different standing wave (depending on the dielectric core content and the depth of the shell).

Plasmonic particles disclosed herein may also have various size ranges. In some embodiments, the plasmonic particles have a dimension (i.e., size) less than approximately 1000 nm. In some embodiments, the plasmonic nanoparticles are plasmonic nanoparticles that have a size between approximately 1 nm and approximately 100 nm. In some embodiments, the plasmonic particles have a size between approximately 0.5 nm and approximately 200 nm. In some embodiments, the plasmonic nanoparticles may have a size in the range of approximately 5 nm to approximately 30 nm. In some embodiments, the plasmonic nanoparticles have a size between approximately 2 nm and approximately 20 nm. Plasmonic nanoparticles disclosed herein may or may not exhibit size-related properties that differ significantly from those observed in fine particles or bulk materials.

In various embodiments, plasmonic particles may also include a functionalized surface. For instance, FIG. 3A depicts plasmonic particle 42 with functionalized surface 44 that contains functional groups 46. In some embodiments, the functionalized surface may include hydrophilic functional groups, hydrophobic functional groups, anionic functional groups, cationic functional groups, and/or zwitterionic functional groups. In some embodiments, the functionalized surface may also include functional groups derived from carboxylic acids, esters, amines, alcohols, alkanes, aryl groups, and combinations thereof. In some embodiments, the surfaces of plasmonic particles may be functionalized by various amino acids. Non-limiting examples include glutamic acid, lysine, and cysteic acid.

Without being bound by theory, it is believed that functional groups on the surface of plasmonic particles contribute to the solubility of the particles in the mobile phase, as well as in various solvents. For instance, in various embodiments, the surface functionalization of plasmonic particles may be chosen to promote the solubility or miscibility of the plasmonic particles in a desired solvent, such as a solvent with a desired pH and/or ionic concentration. In some embodiments, the solubility or miscibility of the plasmonic particles may be chosen to either promote solubility in water or in hydrocarbons. In some embodiments, the functional groups on the plasmonic particles may be chosen to promote high transport through a specific rock formation, but not through other formations.

The functional groups on the surface of plasmonic particles may also contribute to the absorbance characteristics of the particles onto the immobile phase. As such, the functional groups on the plasmonic particles may also be chosen to promote absorbance onto a specific rock formation, but not onto other formations.

Various techniques may also be used to tailor the choice of functional groups on plasmonic particles in order to ensure a desired solubility or immobile phase absorbance. For example, water solubility may be attained through the use of substituents that promote hydrogen bonding. See, e.g., R. L. Callender et al., Aqueous synthesis of water soluble alumoxanes: environmentally benign precursors to alumina and aluminum-based ceramics, *Chem. Mater.*, 1997, 9, 2418. Also see C. D. Jones et al., Synthesis and characterization of carboxylate-FeOOH nanoparticles (ferroxanes) and ferroxane-derived ceramics, *Chem. Mater.*, 2002, 14, 621. In some embodiments, water solubility may be attained through the use of charged substituents. See, e.g., L. Zeng et al., Tailoring aqueous solubility of functionalized single-wall carbon nanotubes over a wide pH range through substituent chain length, *Nano Lett.*, 2005, 5, 2001. In some embodiments, the use of hydrophobic substituents allows for solubility within organic solvents. See, e.g., C. C. Landry et al., From minerals to materials: synthesis of alumoxanes from the reaction of boehmite with carboxylic acids, *J. Mater. Chem.*, 1995, 5, 331.

Plasmonic particles disclosed herein may also have various shapes. For instance, in some embodiments, the plasmonic particles may be rod-like particles, spheroidal particles, oval shaped particles, and/or circular particles.

The shapes of plasmonic particles can confer various benefits. For instance, in the case of gold particles, a stronger SPR effect has been observed with gold rods. In addition, the number of peaks generally increases as the symmetry of the particles decreases. This is evident in the SPR spectra of materials containing prolate spheroidal particles.

Plasmonic particles disclosed herein may be dissolved or suspended in various mobile phases to form plasmonic particles solutions. Mobile phases may be any solvent or solution that can solubilize or dissolve plasmonic particles. In some embodiments, the mobile phase may be water, hydrocarbons, or mixtures thereof. In some embodiments, the mobile phase is water with a pH that is comparable to that found in a subterranean reservoir or used during a recovery process, such as a water flood or a hydraulic fracture. In some embodiments, the mobile phase is water with a pH range of approximately 2 to approximately 11.

In some embodiments, the mobile phase may comprise ionic compounds. Without being bound by theory, such ionic compounds may aid in the control of the ionic strength of the mobile phase. In some embodiments, the ionic compounds may comprise at least one of alkali metals, alkaline earth metals, halides, and carbonates. Various concentrations of ionic compounds may also be utilized. For instance, in some embodiments, the ionic compounds may have a concentration range between 0.1 M and 0.5 M.

In some embodiments, the mobile phase may have at least one of surfactants or colloids. In various embodiments, such surfactants or colloids may be any chemical compositions containing aliphatic acids, aliphatic alcohols, glycol ethers, alkyl aryl polyethoxy ethers, alkyl aryl polyethoxy ethanol, alkyl aryl sulfonates, aromatic hydrocarbons, aromatic ketones, oxyalkylated compounds, alkyl phenols, petroleum blends, polyethoxylated alkanols, polymeric hydrocarbons, salt of amine-carbonyl condensates, salts of fatty acids, polyamine reaction products, carbohydrates, industrial surfactant blends, and mixtures thereof. In some embodiments, the surfactants or colloids may include mercaptosuccinic acid (MSA), 2-aminoethanthiol, 11-mercapto-lundecanol, and combinations thereof. Such constituents may be mixed with the mobile phase at various concentrations and ratios.

In various embodiments, the mobile phase is a premixed stock solution. In some embodiments, the premixed stock solution may contain aqueous or organic solvents, salts, carbonates, acids, and/or bases. In some embodiments, the premixed stock solution may contain other particles or compounds that may be encountered or be of interest when studying nanoparticle mobility through subterranean environments. These may include, without limitation, shales, carbonates, clays, silicates, and other geologic particulates.

Mineral Formations and Immobile Phases

Embodiments of the present invention may be applied to various mineral formations that comprise an immobile phase. Examples of such mineral formations include, without limitation, subterranean reservoirs, oil and gas wells, aquifers, source rocks, top soils, sand deposits, porous man-made structures such as concrete and asphalt barriers, and the like.

In some embodiments, reservoir types include, without limitation, carbonates, silicates, tight, water drives, retrograde gas condensates, water drive oil, heavy oil, and light oil.

In some embodiments, the immobile phase may be the mineral formation in its native state. In some embodiments, the immobile phase may be an isolated composition that comprises one or more components of a mineral formation or a reservoir (e.g., an oil or gas reservoir). For instance, in some embodiments, the immobile phase may include one or more minerals found in subterranean reservoirs, such as aluminates, silicates, carbonates, sulfates, sulfides, and the like. In some embodiments, the immobile phase may comprise one or more of the following subterranean reservoir components: sands, sandstones, shales, micas, clays, rocks, and combinations thereof.

The immobile phase may have many formations, sizes, and compositions. In some embodiments, the immobile phase has a generally uniform size, a uniform porosity, and a known volume. For instance, in some embodiments, the immobile phase has a particle size range of between approximately 1 micrometer in diameter to approximately 100 micrometers in diameter. In some embodiments, the immobile phase has a particle size range of between approximately 10 micrometers in diameter to approximately 50 micrometers in diameter.

In some embodiments, the immobile phase is packed in a column, such as the immobile phase column 26 shown in FIG. 2. Such a column may be a sample core from the reservoir, or it may represent a simulation of the contents of the reservoir. In some embodiments, the column comprises an inert material, such as nylons, glasses, plastics, metals, and combinations thereof. Additional suitable columns can also be envisioned by persons of ordinary skill in the art.

Flowing Plasmonic Particles Solutions onto Immobile Phases

Various methods may be used to flow plasmonic particles solutions onto immobile phases. In some embodiments, such methods comprise injecting plasmonic particles solutions into an immobile phase. In some embodiments, such methods comprise flushing the plasmonic particles solution through the immobile phase. For example, the plasmonic particles solution may be injected through a well bore of the subject reservoir. An embodiment of such a process may include combining the plasmonic particles solution with hydraulic fracturing fluid or drilling mud.

Various apparatus may also be used to flow plasmonic particles solutions onto immobile phases. An example of a suitable apparatus is shown as apparatus 10 in FIG. 2, as previously described above. Other suitable apparatus can also be envisioned by persons of ordinary skill in the art.

Various flow rates may also be utilized. For instance, in some embodiments, the plasmonic nanoparticles may be flushed or injected into immobile phases at flow rates in the range of between approximately 5 mL/min to approximately 50 mL/min. In some embodiments, the flow rate may remain constant. In some embodiments, the flow rate may fluctuate.

Absorbance of Plasmonic Particles on Immobile Phases

The absorbance of plasmonic particles onto immobile phases may be determined by various methods. In some embodiments, the absorbance determination involves comparing the determined absorbance of the plasmonic particles solution before the above-mentioned flowing process (i.e., before flowing the plasmonic particles solution onto an immobile phase) with the determined absorbance of the plasmonic particles solution after the flowing process (i.e., after the plasmonic particles solution is eluted from the immobile phase). As noted above, and further below, with respect to FIG. 36, a difference in trends between the absorbance curves can be used to determine how the plasmonic particles deposit onto the contents in the immobile phase.

In some embodiments, the absorbance of the plasmonic particles solutions before and after the flowing process are determined by a UV-detector, such as a UV-visible spectrophotometer. In some embodiments, the absorbance of the plasmonic particles solutions are determined as a function of time.

In some embodiments, the absorbance of the plasmonic particles solutions are determined at a wavelength characteristic of the most intense plasmon resonance of the plasmonic particle. In some embodiments, the absorbance of the plasmonic particles solutions are determined at a wavelength range of between approximately 300 nm and approximately 500 nm.

In some embodiments, the absorbance of plasmonic particles onto immobile phases is determined by determining the sticking coefficient of the plasmonic particles onto the immobile phase. In some embodiments, the following formula may be used to determine the sticking coefficient:

$$\alpha = -\frac{2d_C}{3(1-\epsilon)\eta_0 L}\ln(C/C_0)$$

In this formula, $\alpha$ is the attachment efficiency factor, $d_c$ is the diameter of a collector in the porous medium or immobile phase, $\epsilon$ is the porosity of the medium, $C$ and $C_0$ are respectively the particle concentrations present at distance L and at L=0, and $\eta_0$ is the clean bed single collector efficiency that describes the particle transport to an individual collector geometry. See R. Yao et al., *Environ. Sci. Technol.* 1971, 5, 1105.

In addition, the clean bed collector efficiency can be determined as a function of the Darcy velocity, porous medium grain size, porosity, and temperature among other variables. See N. Tufenkji et al., *Environ. Sci. Technol.* 2004, 38, 529.

In some embodiments, the attachment efficiency may be treated as an empirical parameter that captures all aspects of particle deposition not described by the more extensively validated particle transport models, assuming that sequential steps of transport and attachment are adequate to describe particle deposition. In addition, a mass balance of particles $C/C_0$ over a differential volume of porous medium can be integrated over distance L within a homogeneous medium to yield an expression for the attachment efficiency factor.

In some embodiments, experimental a values can be determined for a given particle suspension using experimental $C/C_0$ values (fraction of in-fluent particles remaining) and theoretical $\eta_0$ values. Theoretically, values of the attachment efficiency determined from data obtained from experiments with one porous medium can be applied to another porous medium of similar composition but different grain size, fluid flow rate, and porosity. Although the validity of interpreting $C/C_0$ data to obtain an estimate of attachment efficiency has been established for nanoscale particles, this assumption has not yet been evaluated for engineered nanoparticles. See J. E. Tobiason et al., *J. Am. Water Works Assoc.* 1988, 80, 54.

By way of information, and without being bound by theory, the relative mobility of a particle passing through a porous medium is linked to its tendency to deposit on immobile surfaces. Particles are transported to the surface of a collector when their encompassing solvent pass sufficiently close to the collector surface such that particles make contact with the surface. See J. Happel, *AIChE J.* 1958, 4, 197. Particles may also contact collectors due to the effects of gravity or Brownian diffusion. Transport nanoparticles are generally dominated by Brownian diffusion. Forces such as the London forces, van der Waals forces, and double-layer forces are typically considered as influencing particle attachment rather than transport. See, e.g., Derjaguin et al., *USSR Acta Physicochim.* 1941, 14, 633. Also see E. J. W. Verwey et al., *Theory of the stability of Lyophobic Colloids;* Elsevier: Amsterdam, 1948.

Particle trajectory calculations have been combined with the analytical solution for Brownian transport to yield closed-form solutions for the transport of particles to the surface of spherical collectors. See R. Rajagopalan et al., *AIChe J.,* 1976, 22, 523. Such calculations are expressed as the theoretical single collector efficiency $\eta_0$. Data for the deposition of particles varying in size over several orders of magnitude (including particles dominated by Brownian transport) has been found to be adequately represented by this model for particle transport when conditions favor particle attachment. See K. M. Yao et al., *Environ. Sci. Technol.,* 1971, 5, 1105. However, when particle attachment is not favorable, only a fraction of the collisions with the collector surface will result in particle deposition, and the single collector efficiency is typically modified.

The ratio of the rate of particle deposition on a collector to the rate of collisions with that collector is referred to as the collision efficiency or attachment efficiency factor, $\eta_r$. The attachment efficiency is a function of numerous phenomena, including van der Waals forces, electrical double-layer interactions, steric interactions, hydration forces, and particle/surface hydrophobicity. The value of $\eta_r$ is unity when there are no barriers to particle deposition and attachment is favored but may exceed one if phenomena at small separation distances draw particles to the surface. See M. Elimelech, *J. Colloid Interface Sci.,* 1994, 164, 190. Particle transport and attachment are often represented as the product of the attachment efficiency and the collector efficiency: $\eta_r = \alpha \, \eta_0$ Models such as DLVO theory, which consider the net particle interaction potential as a function of distance separating particles and collector surfaces due to London-van der Waals forces and electric double-layer interaction forces, suggest that particle attachment under unfavorable conditions should be a strong function of particle size and ionic strength. However, experimental evidence does not support these predictions. Moreover, models describing attachment efficiency, such as those that consider the balance between electrostatic and van der Waals forces, typically describe changes over length scales that may be many nanometers in size. Similarly, structural or hydration forces and steric interactions that affect particle stability may be effective over length scales that are large by comparison with some nanoparticle dimensions. Extensions or modifications of current theory may be needed to describe the attachment efficiency for some smaller nanomaterials.

Embodiments of the present invention may have numerous applications. For instance, some embodiments of the present invention may be used to determine the suitable surface functionalization, particle size, and particle shape of plasmonic particles to be used as a tracer or contrast agent for down-hole applications in a particular mineral or rock formation. Embodiments of the present invention may also be used to determine the behavior of plasmonic nanoparticle functional groups under various downhole conditions, including conditions of varying pH, ionic strength, and solvent.

Embodiments of the present invention may also be used to determine the suitable functional group on a nanoparticle that will be used to track and/or trace the characteristics of mineral or rock formation or a proppant pack. Such characteristics may include fracture height, fracture width, fracture depth, and fracture trajectory.

Embodiments of the present invention may also be used to determine the suitable functionalization of a nanoparticle to allow for the accurate assessment of the geometry of a subterranean fracture. Such applications may allow for accurate determination of the transport of nanoparticles through rock formations under various conditions employed downhole in the oil and gas industry.

Embodiments of the present invention also have numerous advantages. For instance, one of the advantages is that the mobility of a nanoparticle through a mineral stationary phase can be determined under conditions of temperature, concentration, pH, and salinity that are found in the downhole environment. A further advantage is that the enhanced detection of the plasmon nanoparticles over the types of nanoparticles intended for downhole use allows for the measurement of the fine structure of the flow characteristics.

Various embodiments of the present invention will now be described with respect to the Examples below.

EXAMPLES

Example 1

Synthesis of Silver Nanoparticles

The method used for the synthesis of silver nanoparticles in this Example employed a modified Lee and Meisel method. See P. C. Lee et al., Absorption and surface-enhanced Raman of dyes on silver and gold sols, *J. Phys. Chem.,* 1982, 86, 3391. In particular, the method utilized a reduction technique with silver nitrate as the metal precursor. Silver nitrate was reduced by sodium borohydride and mercaptosuccinic acid (MSA) as a capping ligand. The synthesis may be carried out in a solvent of pure water, organic materials such as methanol, or a combination.

Approximately 100 mL of a 0.3 M solution of MSA was added to approximately 100 mL of a 1.2 M solution of silver nitrate using a magnetic stir bar to create agitation. To this mixture, approximately 25 mL of a 0.2 M sodium borohydride solution was added slowly, taking care not to increase the pH sharply, which would result in the silver precipitating from solution. The color changed very rapidly from a clear solution to a light yellow, then dark yellow, brown, and then black. To ensure product quality, the reaction was kept covered. This prevented reduction or oxidation of the silver ions arising from stray light. The reaction was carried out at room temperature.

The above method had several variations. Such variations are described below as Method 1, Method 2, and Method 3.

Method 1. The total volume of the reaction was approximately 200 mL in distilled water. MSA and $AgNO_3$ were placed in a stirring Erlenmeyer flask. NaBH$_4$ was then added to the stirring solution. The solution turned yellow, then brown, and then black. The reaction was left to stir for 2 hours at room temperature. The glassware was covered with foil. After 2 hours, the solution was centrifuged for 15 minutes at 4400 rpm. The supernatant was discarded, and the pellet was re-suspended in DI water with the aid of light bath sonication.

Method 2. 2-Aminoethanethiol hydrochloride (AET) was used in conjunction with MSA. Sample preparation was identical to Method 1.

Method 3. 11-mercapto-1-undecanol was used in conjunction with MSA. Sample preparation was identical to method 1.

Table 1 summarizes the different reactions conditions used in Example 1, as previously described.

TABLE 1

| Method | AgNO$_3$ (g) | Surfactant (g) | NaBH$_4$ (g) |
|---|---|---|---|
| Method 1 | 0.204 | 0.150 | 0.3783 |
| Method 1 | 0.204 | 0.450 | 0.3783 |
| Method 1 | 0.204 | 0.751 | 0.3783 |
| Method 1 | 0.410 | 0.450 | 0.3783 |
| Method 2 | 0.204 | 0.450 + 0.056 | 0.3783 |
| Method 2 | 0.204 | 0.450 + 0.114 | 0.3783 |
| Method 3 | 0.204 | 0.341 | 0.3783 |
| Method 3 | 0.204 | 0.613 | 0.3783 |
| Method 3 | 0.204 | 0.102 | 0.3783 |

Figure 7:
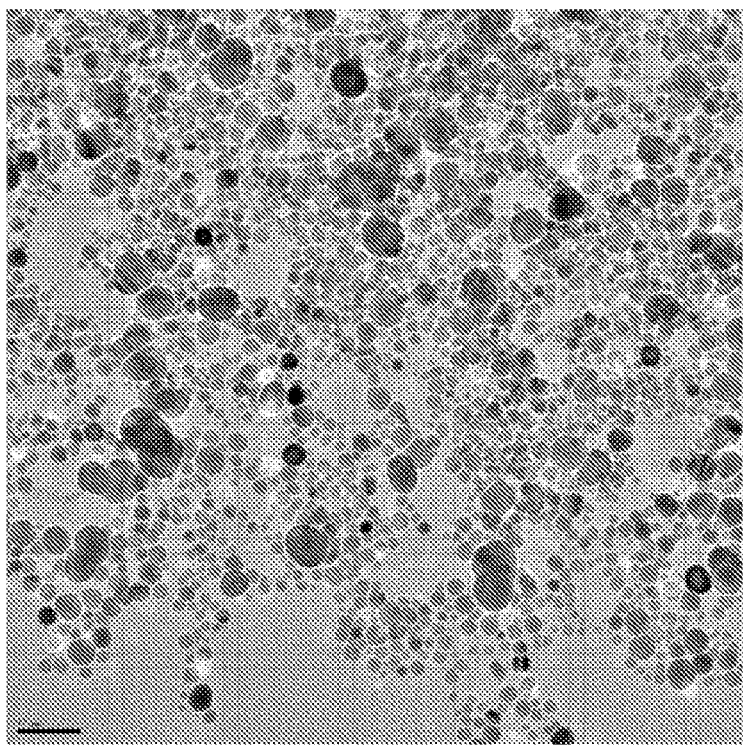
FIG. 7 is a TEM image of silver nanoparticles made in accordance with Method 1 (as described in Example 1). The scale bar is 50 nm.
Figure 8:
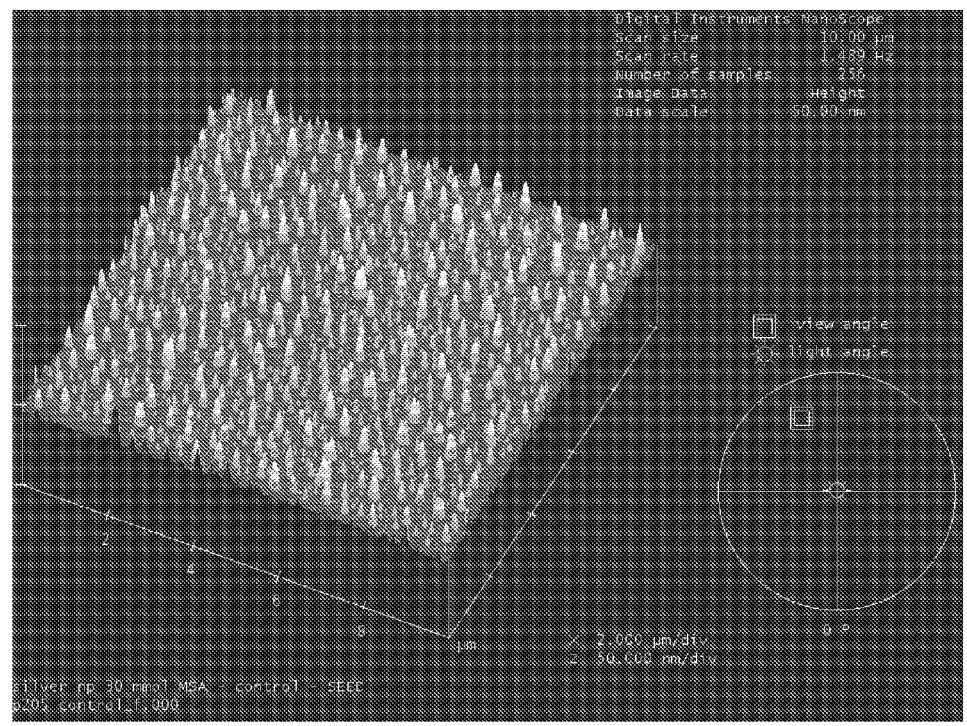
FIG. 8 is a perspective view of an atomic force microscopy (AFM) image of silver nanoparticles. The nanoparticles were made in accordance with Method 1 (as described in Example 1).
Figure 9:
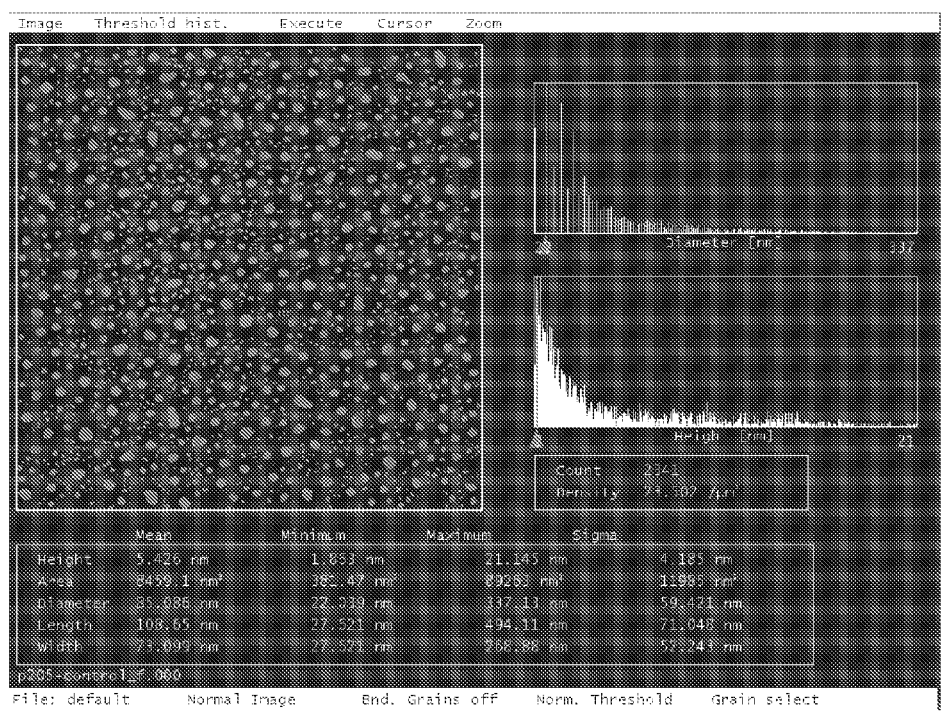
FIG. 9 shows particle analysis of silver nanoparticles conducted using AFM. The nanoparticles were made in accordance with Method 1 (as described in Example 1).

The particles were characterized by a combination of Atomic force microscopy (AFM), Transmission electron microscopy (TEM), Small angle X-ray scattering (SAXS) and UV-vis spectroscopy. FIG. 7 is a TEM image of silver nanoparticles made in accordance with Method 1. The scale bar is 50 nm. FIG. 8 is a perspective view of an atomic force microscopy (AFM) image of the silver nanoparticles. FIG. 9 shows particle analysis of the silver nanoparticles conducted using AFM.

Figure 14:
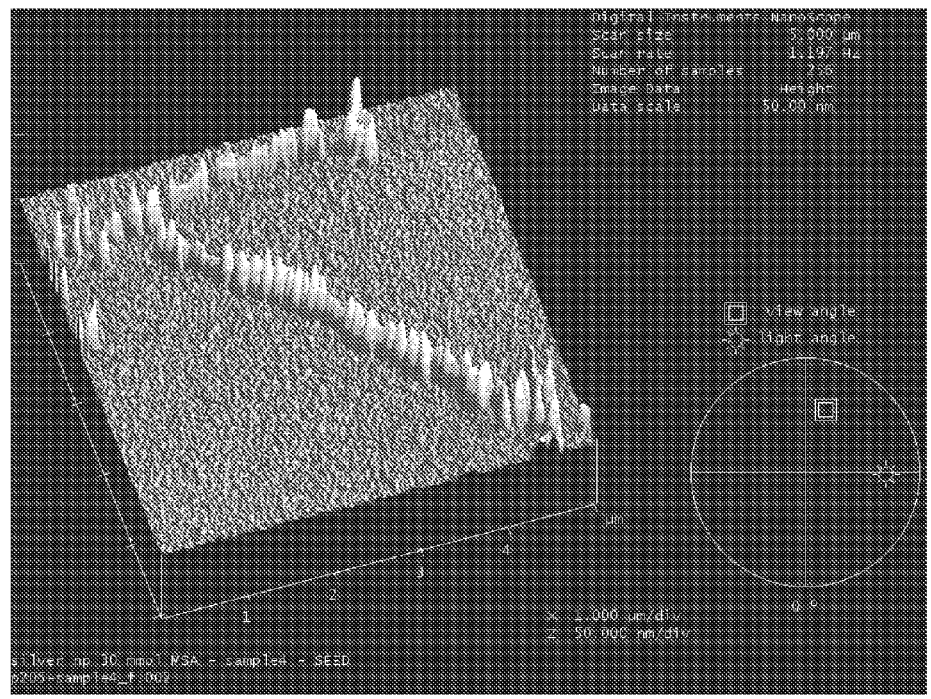
FIG. 14 is an AFM image of silver nanoparticles that are cross-linked with each other due to the pH of the solution. The nanoparticles used in this example are end terminated with the carboxyl groups of the MSA. The nanoparticles were made in accordance with Method 1 (as described in Example 1).

More specifically, the particles were characterized by AFM in tapping mode with the sample drop cast onto a newly cleaved mica surface and spun down to dryness at 1400 rpm for 2 mins. The results are shown in FIG. 14, which is an AFM image of the silver nanoparticles that are cross-linked with each other due to the pH of the solution. The nanoparticles used in this example are end terminated with the carboxyl groups of the MSA.

Figure 13:
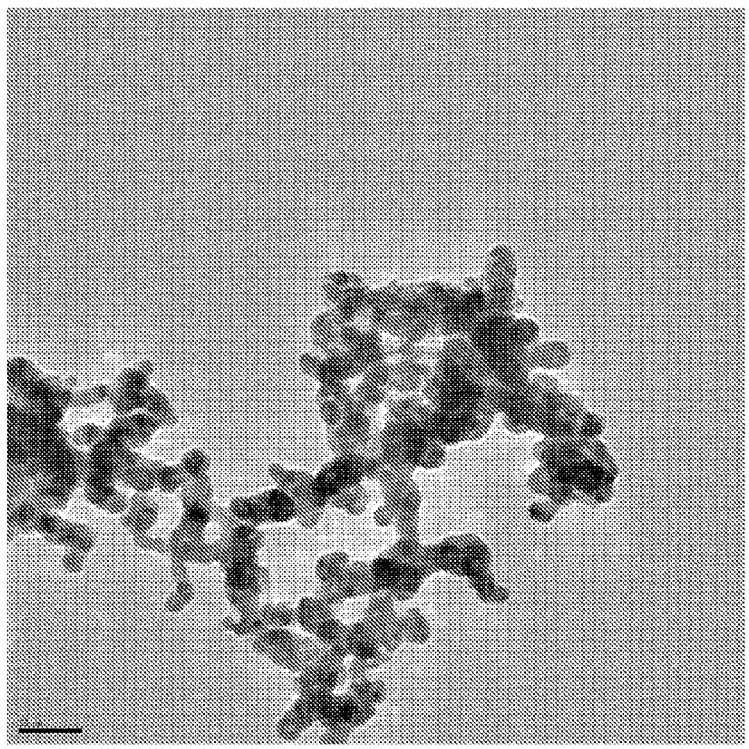
FIG. 13 is a TEM of silver nanoparticles made with a 3:1 ratio of mercaptosuccinic acid (MSA):2-aminoethanethiol (AET). The nanoparticles are fused due to hydrogen bonding of carboxyl groups and amines. Scale bar is 50 nm. The nanoparticles were made in accordance with Method 2 (as described in Example 1).

The particles were analyzed by TEM on a JEOL 1230 HC-TEM at a 120 KV acceleration voltage. The sample was cast onto a copper grid that was coated in amorphous carbon dried in vacuum. The results are shown in FIG. 13, which is a TEM of silver nanoparticles made with a 3:1 ratio of MSA: AET. The nanoparticles are fused due to hydrogen bonding of carboxyl groups and amines. Scale bar is 50 nm. The nanoparticles were made in accordance with Method 2.

Figure 10:
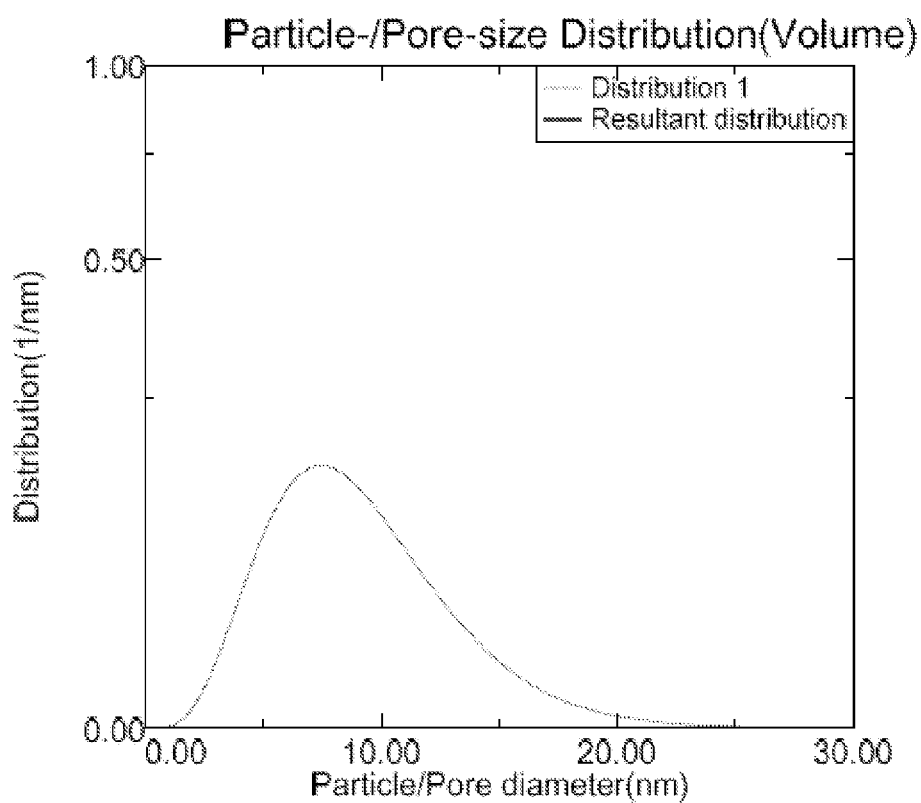
FIG. 10 shows a size distribution of nanoparticles, as determined using small angle X-ray scattering. The nanoparticles were made in accordance with Method 1 (as described in Example 1).

SAXS was conducted on a Rigaku SmartLab X-ray diffractometer with Cu X-ray tube. The sample was mounted in a liquid state onto a capillary tube. The diffuse pattern was analyzed using Nanosolver software. The results are shown in FIG. 10, which shows a size distribution of the nanoparticles as determined using small angle X-ray scattering. The nanoparticles were made in accordance with Method 1.

Figure 11:
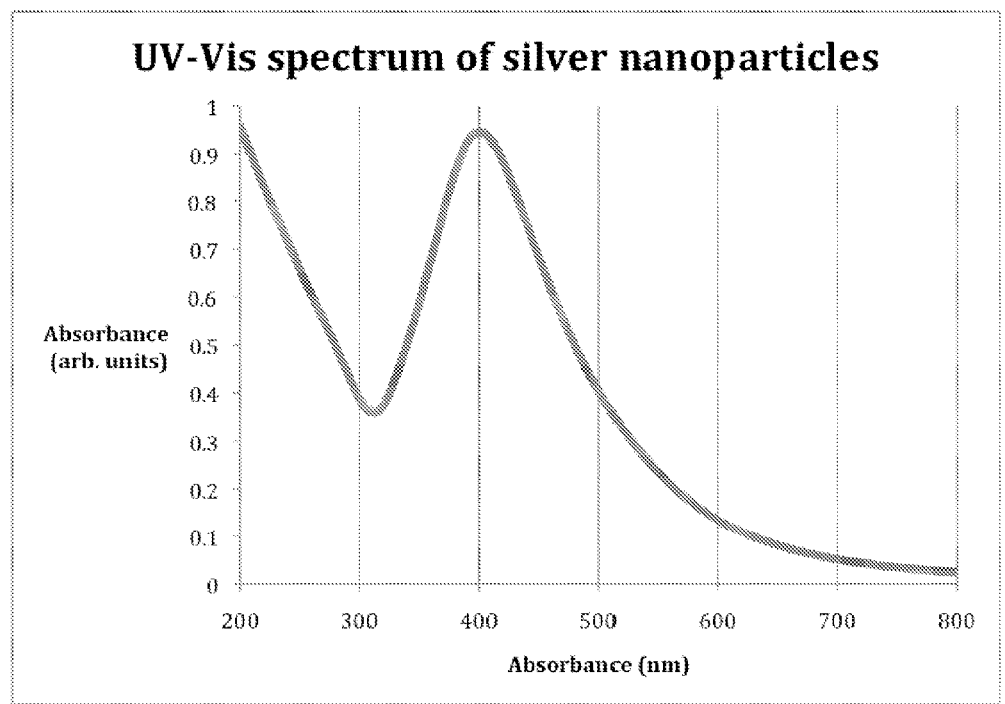
FIG. 11 is a UV-vis spectrum of silver nanoparticles showing strong absorbance at 400 nm. The nanoparticles were made in accordance with Method 1 (as described in Example 1).

UV-VIS spectroscopy was conducted on an Agilent 8453 UV-VIS analyzer. The sample was placed in a cuvette and analyzed from approximately 300 nanometers to approximately 1100 nanometer wavelengths. The results are shown in FIG. 11, which is a UV-vis absorbance spectrum of the silver nanoparticles showing strong absorbance at 400 nm. The nanoparticles were made in accordance with Method 1.

Figure 12:
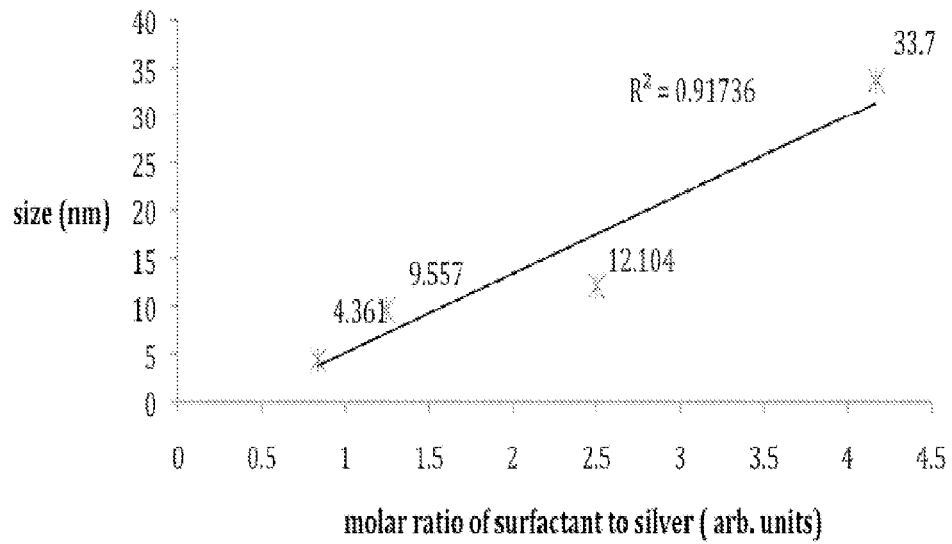
FIG. 12 is a graph showing a change in nanoparticle mean diameter as a function of reagent concentration (i.e., the molar ratio of surfactant to that of silver). The nanoparticles were made in accordance with Method 1 (as described in Example 1).

Control of the particle size was achieved by variation of the molar ratio of surfactant to the molar amount of silver ([S]/[Ag]). Increasing concentrations of the capping ligand created larger nanoparticles due to the formation of larger micelles in solution. Increasing the relative silver concentration decreased particle sizes, primarily due to the increased number of nucleation sites that seeded nanoparticle growth. See V. T. Liveriri, "*Controlled Synthesis of Nanoparticles in Microheterogeneuos Systems*", Springer: New York, 2006. This method consistently made monodispersed uniform particles with a mean diameter of less than 30 nm, primarily due to the strong reducing agent that was employed. See FIG. 12, which is a graph showing a change in nanoparticle mean diameter as a function of reagent concentration (i.e., the molar ratio of surfactant to that of silver). The nanoparticles were made in accordance with Method 1.

Solubility in both organic and aqueous environments was possible through the use of MSA. In addition, a short alkane chain (0.6 nm) on the ligand can afford favorable interactions with organic solvents, such as methanol. See K. Kimura et al., "Self-Assembling of Gold and Silver Nanoparticles at a Hydrophilic/Hydrophobic Interface: A Synthetic Aspect and Superstructure Formation," *Synth. React. Inorganic, Metal-Organic, Nano-Metal Chem.*, 2006, 36, 237. Likewise, two carboxylic acids can give ample opportunity for hydrogen bonding to the surrounding water molecules, making the particles soluble in aqueous media and some polar organic solvents. Another strategy to control nanoparticle interactions with other media incorporates the use of a ligand with a different functional group, such as an amine or an alcohol. To achieve this, the nanoparticles were made AET hydrochloride or 11-mercatoundecanol in place of MSA.

The colloidal dispersion in aqueous environments of both the carboxyl and the amine-terminated nanoparticles are subject to the solution pH. There is a pH dependence on the samples due to the possibility for interparticle binding when the pH is larger than the pKa of the terminal functional group. For instance, at pH 4, it was shown that the carboxyl-terminated nanoparticles could be linked together and imaged under AFM. See FIG. 14.

Example 2

Analysis of the Flow of Silver Nanoparticles through Immobile Phases

Apparatus 10 shown in FIG. 2 was used to analyze the flow of silver nanoparticles through various immobile phases. An altered version of a Combi flash gear pump companion was used as consolidating container 16. In particular, the electronic three-way flow switch from the gear pump was removed and replaced with a union PEEK ⅛ that bypassed the waste outlet. The tube outlet was disconnected from the dispenser arm and attached to immobile phase column 26, which was then connected to housing 32 containing UV-visible spectrometer 34.

The outlet of the housing was attached to a waste container 40 through tubing 34. Mobile phase container 12 containing a stock solution was connected to consolidating container 16 through tubing 13. The stock solution was used as the base line when calibrating the UV spectrophotometer. It was also used to flush the plasmonic nanoparticle solution through the immobile phase.

Plasmonic nanoparticle container 14 contains a stock solution with a concentration of plasmonic nanoparticles in it. The concentration can vary and is only determined by the accuracy of the UV detector.

Immobile phase 26 may be any mineral or rock for investigation, which is ground to a known size and porosity. It was contained within a Redisep column that is 2 cm in diameter and 6.5 cm in length.

UV detector 34 used in this study was the Agilent 8453 UV-Visible spectrophotometer, which uses a photodiode array (PDA). The software used in computer 36 was the Agilent ChemStation Software (the kinetics version). A summary of a typical set of flow conditions are shown in Table 2.

TABLE 2

| | |
|---|---|
| Samples per run: | 1 |
| Solvent delivery: | Two maintenance-free, valveless metering pumps |
| Certification and compliance: | CE, CSA, IMERC |
| Programmable gradients: | 2 solvent isocratic, linear and/or step gradients; optional 4-solvent capability |
| Flow rate: | 5 to 100 ml/min |
| RediSep Rf column sizes: | 4 g to 330 g |
| Rated pressure: | 50 psi (3.5 bar) |
| Liquid sample loading: | Injection valve to load column directly |
| Solid sample loading: | Solid load cartridge for low-solubility samples |
| On-line UV detection: | Photodiode array absorbance detector (200-360 nm) |
| Fraction collection: | Foxy fraction collector with 144 tube capacity, unlimited rack changes, optional 288 tube capacity |
| Optional tube sizes: | Racks available for 12, 13, 16, 18, and 25 mm tubes, 480 ml bottles, and other containers |
| Power options: | 100/117 VAC, 50/60 Hz; 234 VAC, 50/60 Hz |
| System dimensions (H × W × D): | 49 × 49 × 54 cm |
| Weight: | 27.2 kg |
| Solvent reservoir level sensing: | optional |
| Samples per run: | 1 |
| Solvent delivery: | Two maintenance-free, valveless metering pumps |
| Certification and compliance: | CE, CSA, IMERC |
| Programmable gradients: | 2 solvent isocratic, linear and/or step gradients; optional 4-solvent capability |
| Flow rate: | 5 to 100 mL/min |
| RediSep Rf column sizes: | 4 g to 330 g |
| Rated pressure: | 50 psi (3.5 bar) |
| Liquid sample loading: | Injection valve to load column directly |
| Solid sample loading: | Solid load cartridge for low-solubility samples |
| On-line UV detection: | Photodiode array absorbance detector (200-360 nm) |
| Fraction collection: | Foxy fraction collector with 144 tube capacity, unlimited rack changes, optional 288 tube capacity |
| Optional tube sizes: | Racks available for 12, 13, 16, 18, and 25 mm tubes, 480 mL bottles, and other containers |
| Power options: | 100/117 VAC, 50/60 Hz; 234 VAC, 50/60 Hz |
| System dimensions (H × W × D): | 49 × 49 × 54 cm |
| Weight: | 27.2 kg |
| Solvent reservoir level sensing: | optional |

Apparatus 10 was used to conduct various experiments. These experiments are summarized below.

Figure 28:
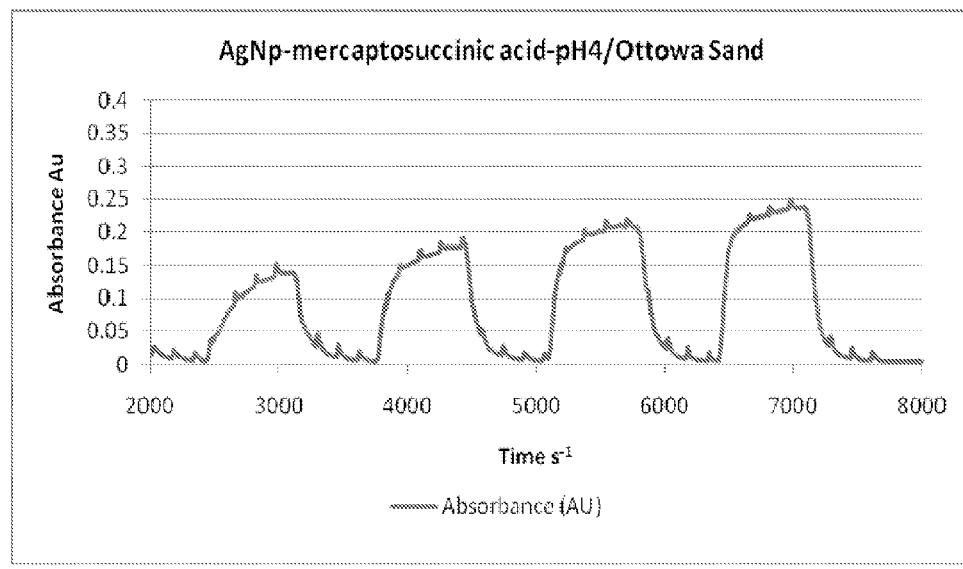
FIG. 28 shows a UV absorbance spectrum of injections of 100% silver nanoparticles capped with mercaptosuccinic acid solution at pH 4. The samples were passed through a column containing Ottawa sand, as illustrated in FIG. 2 and described in Example 2.
Figure 29:
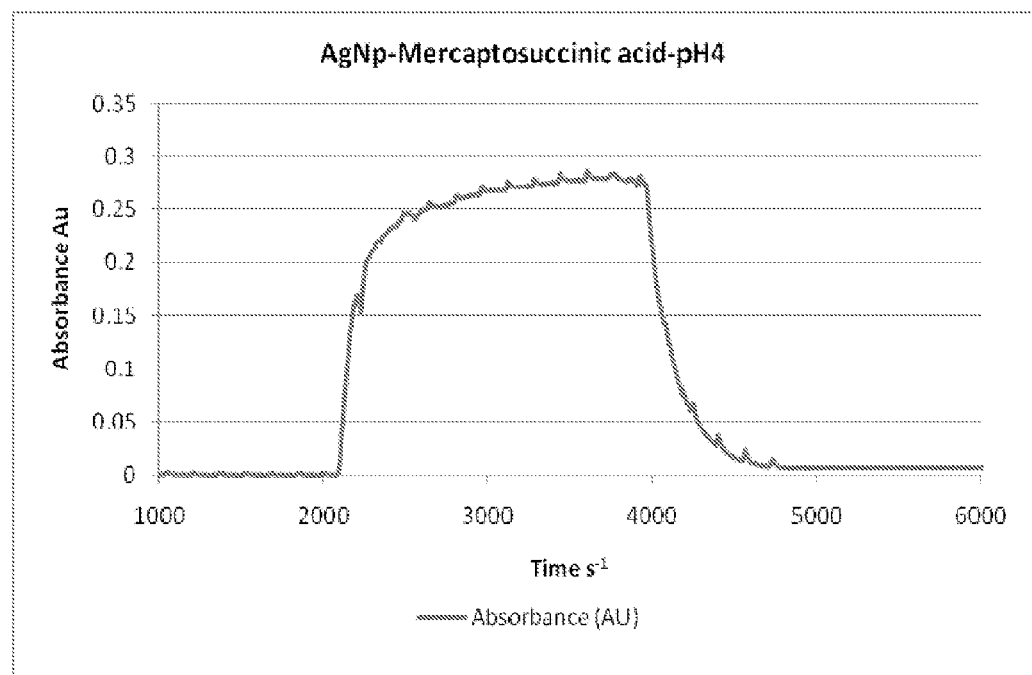
FIG. 29 shows a UV absorbance spectrum of an injection of 100% silver nanoparticle capped with mercaptosuccinic acid solution at pH 4. The sample was passed through a minimal volume tube, as illustrated in FIG. 2 and described in Example 2.

Experiment 1. The software used was Agilent ChemStation (the kinetics version). The software was programmed for a 1 cm cell. Absorbance was programmed to 400 nm absorbance, and for 12,600 seconds. The flow rate was 10 mL min$^{-1}$. HPLC grade Chromosolve $H_2O$ acidified to pH 4 with acetic acid was used as the stock solution. Silver mercaptosuccinic acid capped nanoparticle was used as the plasmonic nanoparticle. The Agilent ChemStation software was programmed to inject approximately 40 mL 100% stock solution for 20 mins. 100% nanoparticle solution was then injected for approximately 20 mins. This was repeated five times. 100% stock solution was washed through the immobile phase column for 30 mins. The procedure was repeated with a 6.5 cm length 2.0 cm diameter Redisep column, containing Ottawa sand. FIG. 28 shows good UV detection, good stable base line, and a stable plateau. FIG. 29 shows UV detection of an injection of the same solution through a minimum volume tube under the same parameters.

Figure 30:
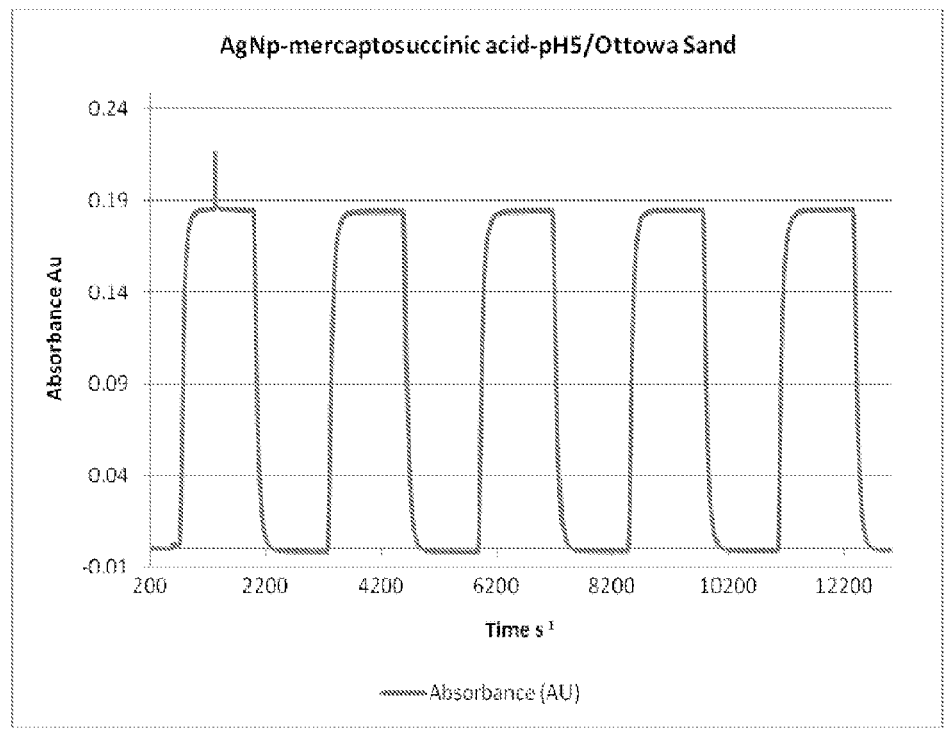
FIG. 30 shows a UV absorbance spectrum of injections of 100% silver nanoparticle capped with mercaptosuccinic acid solution at pH 5 through an Ottawa sand column. The samples were passed through a column containing Ottawa sand, as illustrated in FIG. 2 and described in Example 2.
Figure 31:
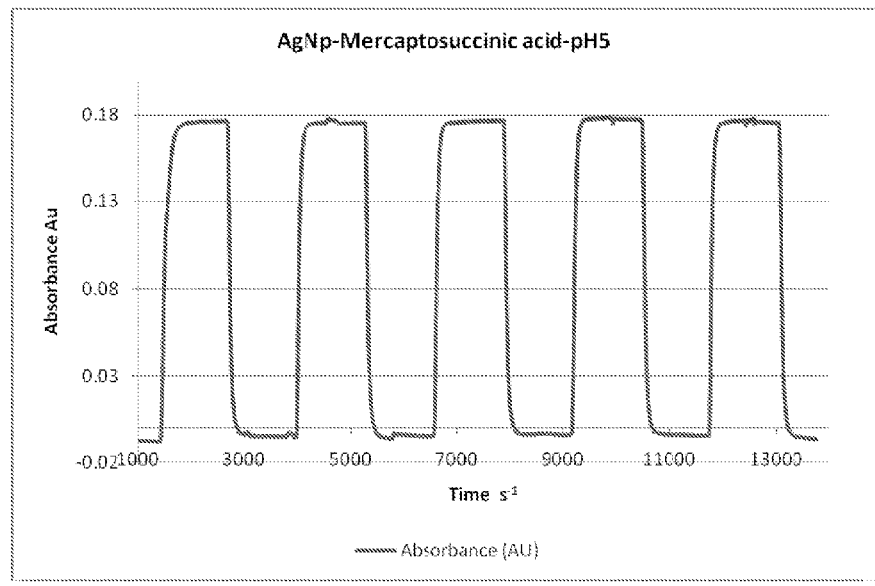
FIG. 31 shows a UV absorbance spectrum of injections of 100% silver nanoparticles capped with mercaptosuccinic acid solution at pH 5. The samples were passed through a minimum volume tube, as illustrated in FIG. 2 and described in Example 2.

Experiment 2. The software used was Agilent ChemStation (the kinetics version). The software was programmed for a 1 cm cell. Absorbance was programmed to 400 nm absorbance, and for 12,600 seconds. The flow rate was approximately 10 mL min$^{-1}$. HPLC grade Chromosolve $H_2O$ acidified to pH 5 with acetic acid was used as stock solution. 24 nm silver marcaptosuccinic acid capped nanoparticle was used as the nanoparticle solution. The Agilent ChemStation software was programmed to inject approximately 40 mL 100% stock solution acidified with acetic acid for approximately 20 mins to pH of 5. 100% nanoparticle solution was then injected for approximately 20 mins. This was repeated five times. 100% stock solution was washed through the immobile phase column for approximately 30 mins. The procedure was repeated with a 6.5 cm length 2.0 cm diameter Redisep column containing Ottawa sand. FIG. 30 shows UV detection of the solution. FIG. 31 shows UV detection of an injection of the same solution through a minimum volume tube under the same parameters.

Figure 32:
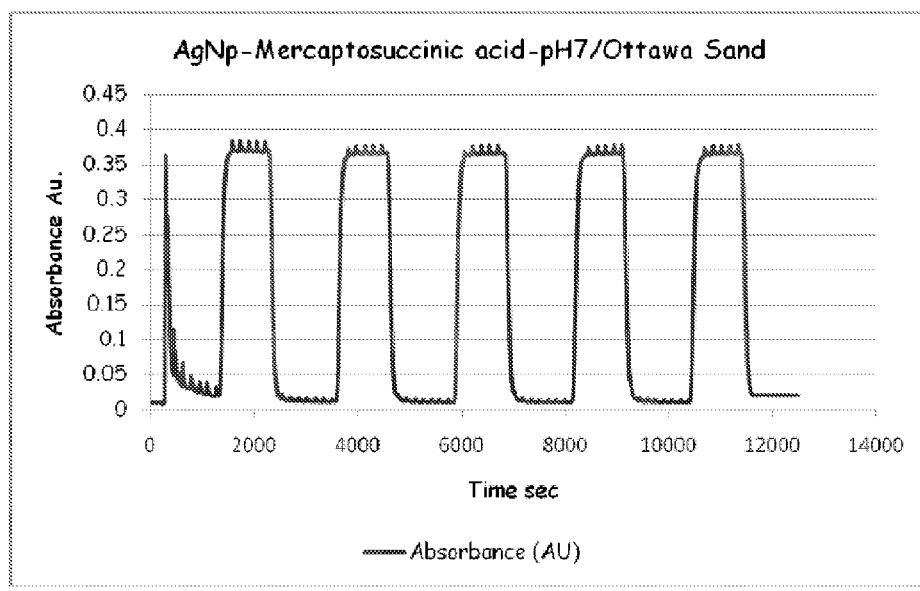
FIG. 32 shows a UV absorbance spectrum of injections of 100% silver nanoparticles capped with mercaptosuccinic acid solution at pH 7. The samples were passed through a column containing Ottawa sand, as illustrated in FIG. 2 and described in Example 2.
Figure 33:
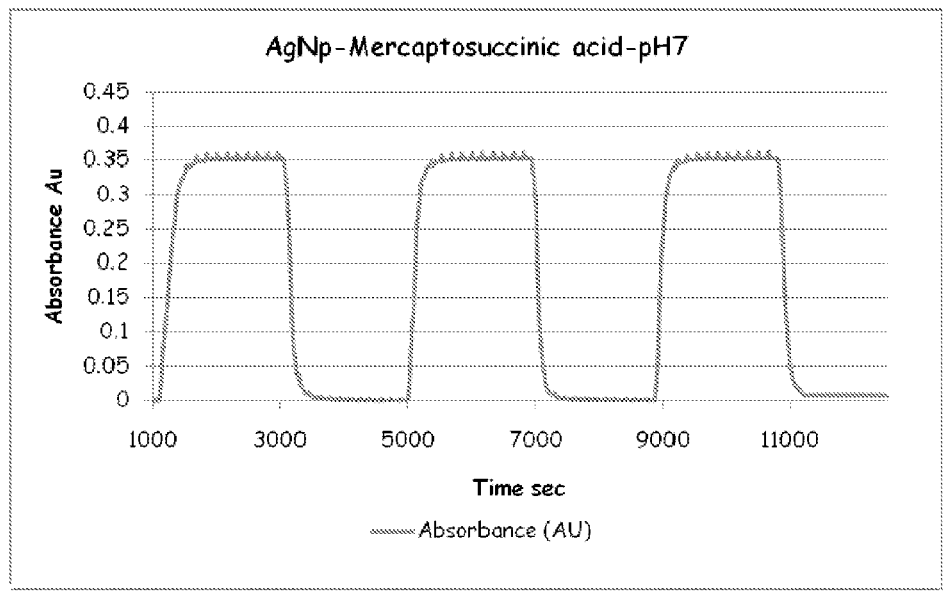
FIG. 33 shows a UV absorbance spectrum of injections of 100% silver nanoparticle capped with mercaptosuccinic acid solution at pH 7. The samples were passed through a minimum volume tube, as illustrated in FIG. 2 and described in Example 2.

Experiment 3. The software used was Agilent ChemStation (the kinetics version). The software was programmed for a 1 cm cell. Absorbance was programmed to 400 nm absorbance, and for 12,600 seconds. The flow rate was approximately 10 mL min$^{-1}$. HPLC grade Chromosolve $H_2O$ acidified was used as a stock solution. 24 nm silver mercaptosuccinic acid capped nanoparticle was used as the nanoparticle solution at pH 7. The Agilent ChemStation software was programmed to inject approximately 40 mL 100% stock solution for approximately 20 mins. 100% nanoparticle solution was then injected for approximately 20 mins. This was repeated five times. 100% stock solution was washed through the immobile phase column for 30 mins. The procedure was repeated with a 6.5 cm length 2.0 cm diameter Redisep column, containing Ottawa sand. FIG. 32 shows good UV detection, good stable base line, and a stable plateau. FIG. 33 shows UV detection of an injection of the same solution through a minimum volume tube under the same parameters.

Figure 34:
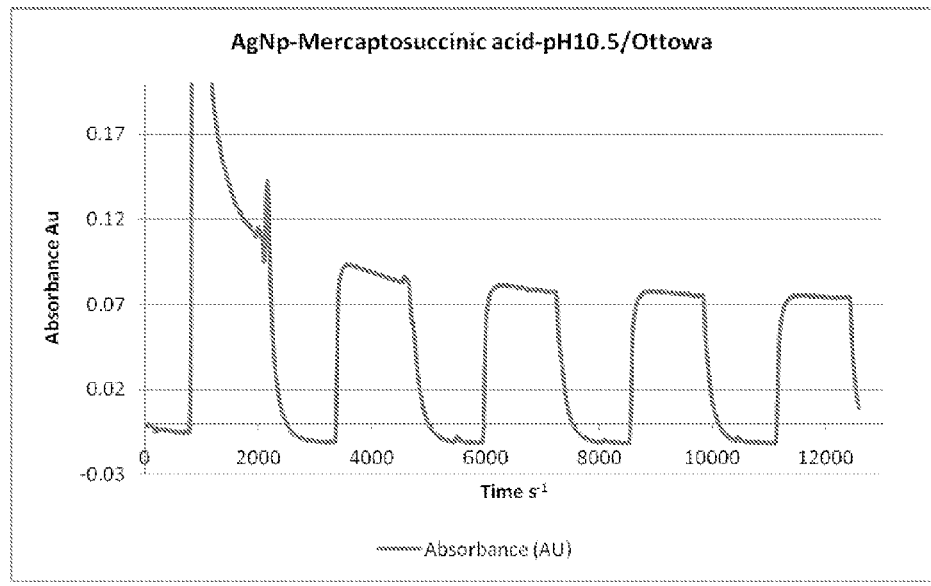
FIG. 34 shows a UV absorbance spectrum of injections of 100% silver nanoparticle capped with mercaptosuccinic acid solution at pH 10.5. The samples were passed through a column containing Ottawa sand, as illustrated in FIG. 2 and described in Example 2.
Figure 35:
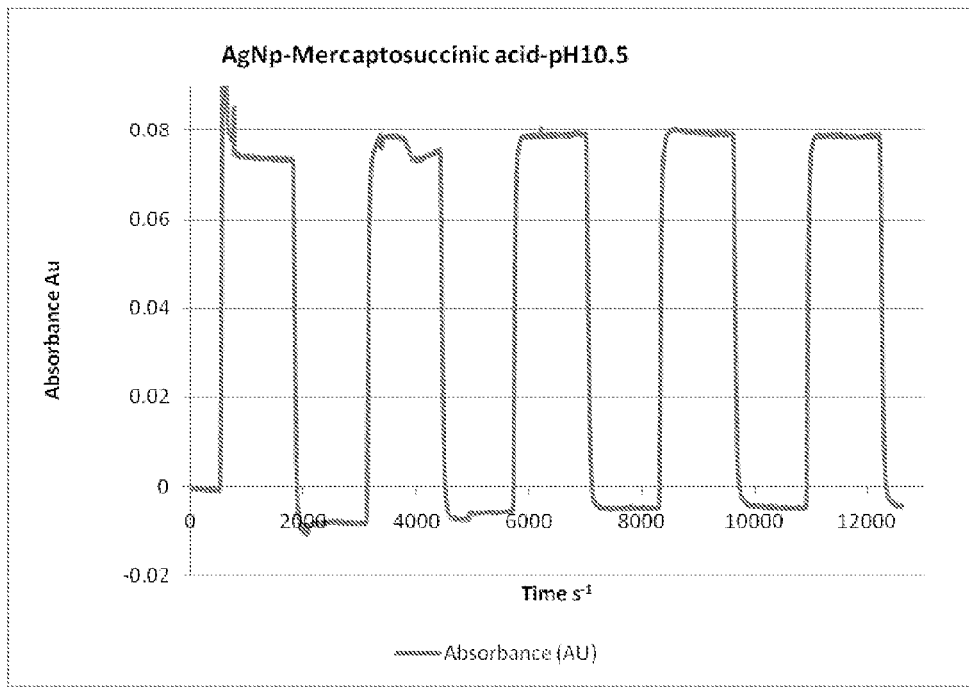
FIG. 35 shows a UV absorbance spectrum of injections of 100% silver nanoparticles capped with mercaptosuccinic acid solution at pH 10.5. The samples were passed through a minimum volume tube, as illustrated in FIG. 2 and described in Example 2

Experiment 4. The software used was Agilent ChemStation (the kinetics version). The software was programmed for a 1 cm cell. Absorbance was programmed to 400 nm absorbance, and for 12,600 seconds. The flow rate was approximately 10 mL min$^{-1}$. HPLC grade Chromosolve $H_2O$ acidified was used as stock solution and adjusted with 1.0 N NaOH soln. to pH 10.5. Silver mercaptosuccinic acid capped nanoparticle was used as the nanoparticle solution. The Agilent ChemStation software was programmed to inject approximately 40 mL 100% stock solution for approximately 20 mins. 100% nanoparticle solution was then injected for approximately 20 mins. This was repeated five times. 100% stock solution was washed through the immobile phase column for approximately 30 mins. The procedure was repeated with a 6.5 cm length 2.0 cm diameter Redisep column, containing Ottawa sand. FIG. 34 shows good UV detection, good stable base line, and a stable plateau. FIG. 35 shows UV detection of an injection of the same solution through a minimum volume tube under the same parameters.

Without further elaboration, it is believed that one skilled in the art can, using the description herein, utilize the present invention to its fullest extent. The embodiments described herein are to be construed as illustrative and not as constraining the remainder of the disclosure in any way whatsoever. While various embodiments have been shown and described, many variations and modifications thereof can be made by one skilled in the art without departing from the spirit and teachings of the invention. The disclosures of all patents, patent applications and publications cited herein are hereby incorporated herein by reference, to the extent that they provide procedural or other details consistent with and supplementary to those set forth herein.

What is claimed is:

1. A method for analyzing a transport of plasmonic particles through a mineral formation comprising an immobile phase, wherein the method comprises:
   (a) dissolving or suspending plasmonic particles in a mobile phase to form a plasmonic particles solution;
   (b) flowing the plasmonic particles solution through the immobile phase;
   (c) determining an absorbance of the plasmonic particles solution, wherein the determining occurs subsequent to flowing the plasmonic particles solution through the immobile phase;
   (d) comparing the determined absorbance of the plasmonic particles solution with an absorbance of the plasmonic particles solution determined previous to flowing the plasmonic particles solution through the immobile phase; and
   (e) determining an absorbance of the plasmonic particles to the immobile phase as a function of the comparison of the determined absorbance of the plasmonic particles solution with the absorbance of the plasmonic particles solution determined previous to flowing the plasmonic particles solution through the immobile phase.

2. The method of claim 1, wherein flowing the plasmonic particles solution through the immobile phase further comprises:
   (a) injecting the plasmonic particles solution into the immobile phase; and
   (b) flushing the plasmonic particles solution through the immobile phase.

3. The method of claim 1, wherein the plasmonic particle is selected from the group consisting of silver particles, gold particles, copper particles, and combinations thereof.

4. The method of claim 1, wherein the plasmonic particle is a nanoshell material comprising a dielectric core surrounded by a shell, wherein the shell comprises at least one of gold, silver, or copper.

5. The method of claim 1, wherein the plasmonic particle comprises a functionalized surface.

6. The method of claim 5, wherein the functionalized surface comprises functional groups selected from the group consisting of carboxylic acids, esters, amines, alcohols, alkanes, aryl groups, and combinations thereof.

7. The method of claim 1, wherein the plasmonic particles have sizes in a range of 0.5 nm to 200 nm.

8. The method of claim 1, wherein the mobile phase comprises hydrocarbons.

9. The method of claim 1, wherein the mobile phase comprises surfactants.

10. The method of claim 1, wherein the immobile phase is a subterranean formation.

11. The method of claim 1, wherein the immobile phase is selected from the group consisting of sands, sandstones, carbonate rocks, shales, micas, aluminates, silicates, clays, and combinations thereof.

12. The method of claim 1, wherein the immobile phase comprises a core extracted from the mineral formation, wherein the core has a particle size range of between approximately 1 micrometer in diameter to approximately 100 micrometers in diameter.

13. The method of claim 1, wherein the immobile phase is packed in a column.

14. The method of claim 1, wherein the mobile phase has a flow rate in a range of between approximately 5 mL/min to approximately 50 mL/min.

15. The method of claim 1, wherein the determining of the absorbance of the plasmonic particles solution is performed using a UV-visible spectrophotometer.

16. The method of claim 1, wherein the determining of the absorbance of the plasmonic particles solution is performed as a function of time.

17. The method of claim 1, wherein determining the absorbance of the plasmonic particle to the immobile phase comprises determining a sticking coefficient of the plasmonic particle to the immobile phase.

18. The method of claim 1, wherein the mineral formation is a subterranean formation.

* * * * *